United States Patent
Omar et al.

(10) Patent No.: US 11,319,292 B2
(45) Date of Patent: May 3, 2022

(54) METABOLICALLY STABLE 5-HMF DERIVATIVES FOR THE TREATMENT OF HYPOXIA

(71) Applicants: King Abdulaziz University, Jeddah (SA); Virginia Commonwealth University, Richmond, VA (US)

(72) Inventors: Abdelsattar Mansour Ebeid Omar, Jeddah (SA); Moustafa El-Sayed El-Araby, Jeddah (SA); Martin K. Safo, Richmond, VA (US)

(73) Assignees: KING ABDULAZIZ UNIVERSITY, Jeddah (SA); VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 17/468,035

(22) Filed: Sep. 7, 2021

(65) Prior Publication Data

US 2021/0403434 A1    Dec. 30, 2021

Related U.S. Application Data

(62) Division of application No. 17/064,998, filed on Oct. 7, 2020, now Pat. No. 11,149,012, which is a division of application No. 16/865,479, filed on May 4, 2020, now Pat. No. 10,836,729.

(51) Int. Cl.
| | |
|---|---|
| *A61P 7/00* | (2006.01) |
| *A61K 31/34* | (2006.01) |
| *C07D 233/64* | (2006.01) |
| *C07D 307/46* | (2006.01) |

(52) U.S. Cl.
CPC ............ *C07D 233/64* (2013.01); *A61K 31/34* (2013.01); *A61P 7/00* (2018.01); *C07D 307/46* (2013.01)

(58) Field of Classification Search
CPC .... C07D 233/64; C07D 307/46; A61K 31/34; A61P 7/00
See application file for complete search history.

(56) References Cited

U.S. PATENT DOCUMENTS

| 2016/0221994 A1* | 8/2016 | Baloglu | ................... A61P 35/00 |
| 2017/0227553 A1* | 8/2017 | Thiele | ..................... G01N 33/60 |

FOREIGN PATENT DOCUMENTS

WO    WO-2018236218 A1  *  12/2018  ........... C07D 307/54

OTHER PUBLICATIONS

Al-Douri et al. "Biogenetic Conversion of Wyerone and Dihydrowyerone into Wyerone Epoxide in Vicia faba Cotyledons and Screening of Antibacterial Activity" J. Chem. 2018 7160205. (Year: 2018).*
Registry No. 1504908-03-5, Chemical Abstract Service, STN Database (online). Entered STN: Dec. 27, 2013. (Year: 2013).*
Fazakerley et al. "Total Synthesis of (+)-Pleuromutilin" Chem. Eur. J. 2013, 19, 6718-6723. (Year: 2013).*

* cited by examiner

*Primary Examiner* — Amanda L. Aguirre
(74) *Attorney, Agent, or Firm* — WC&F IP

(57) ABSTRACT

5-HMF derivative compounds that bind covalently with hemoglobin are provided. Methods of treating sickle cell disease and other hypoxia-related disorders by administering such compounds are also provided.

4 Claims, 11 Drawing Sheets

METABOLICALLY STABLE 5-HMF DERIVATIVES FOR THE TREATMENT OF HYPOXIA

FIELD OF THE INVENTION

The invention is generally related to agents with hypoxic properties for treating disease. In particular, the invention provides hemoglobin-binding Michael Addition compounds with hypoxic properties that are suitable for treating sickle cell disease (SCD), as well as several hypoxia-underlying diseases including, but not limited to, acute respiratory distress syndrome (ARDS), hemorrhagic and traumatic shock, cardiac arrest and cardiogenic shock, traumatic brain injury, stroke, cancer, myocardial infarction, myocardial ischemia, and vaso-occlusive crisis (VOC).

BACKGROUND OF THE INVENTION

Sickle cell disease (SCD) is the most common inherited hematologic disorder affecting over 100,000 people in the U.S. and over 15 million worldwide.[1,2] The number of affected persons is projected to increase by 30% by 2050.[2] SCD results from a single-point hemoglobin (Hb) mutation: βGlu6→βVal6 that changes normal Hb (HbA) into sickle Hb (HbS). Under hypoxic conditions, deoxygenated HbS (Deoxy-HbS) polymerizes into long, rigid fibers, causing sickling of red blood cells (RBCs). The low oxygen affinity (low $O_2$-affinity) of HbS, presumably due to elevation of the natural Hb allosteric effector, 2,3-diphosphoglycerate (2,3-DPG) and/or S1P exacerbates the hypoxia-induced polymerization exacerbates the hypoxia-induced polymerization.[3-9] While the primary interaction in HbS fiber formation occurs between the βVal6 residue and a hydrophobic pocket on an adjacent HbS tetramer, stability of the fiber requires additional intermolecular interactions between the HbS tetramers.[10-15] The rigid RBCs impair blood flow, causing hemolysis and vaso-occlusion, which leads to a cascade of secondary adverse effects, e.g., adhesion of RBCs to tissue endothelium, hemolysis, oxidative stress, decreased vascular nitric oxide (NO) bioavailability, inflammation, painful VOC crisis, and eventually chronic endothelial and organ damage that ultimately leads to poor quality of life and decreased life expectancy.[1,2,16-18]

Until recently, Hydroxyurea (HU), which induces fetal Hb (HbF) production was the only approved drug for treating SCD[19]. HbF modulates clinical severity of SCD by directly inhibiting HbS polymerization. However, a reported lack of response to HU in up to 30% of patients and perhaps, poor compliance, tend to limit its use.[20,21] The past few years have seen three new drugs approved by the FDA for the treatment of SCD. These include L-glutamine (Endari) in 2017 to treat SCD in the US, however, the European regulatory body recommended against approval of the medication due to limited evidence of efficacy in Phase III trials.[22,23] L-glutamine increases the amount of reduced form nicotinamide adenine dinucleotide (NADH) in erythrocytes, which may allow sickle RBCs to more appropriately maintain homeostasis in the face of abundant oxidative stress, and could result in fewer painful crises and adverse events.[24] In 2019, Crizanlizumab (Adakveo)[25] and Voxelotor[26] (Oxbryta, aka GBT440) were approved. Crizanlizumab is a first-in-class monoclonal antibody targeting P-selectin, which is implicated in the pathologic endothelial adhesion of sickle erythrocytes and leukocytes, and has been shown in clinical trials to reduce the frequency of painful vaso-occlusive crises.[25] The anti-sickling agent, Voxelotor was first of a new class of aromatic aldehyde-containing compounds (AEHs) that binds to Hb to prevent HbS polymerization by increasing Hb oxygen ($O_2$) affinity with concomitant antisickling effect.[27-30]

Hemoglobin (Hb) functions in equilibrium between the unliganded or deoxygenated (Deoxy) tense (T) state, which exhibits low affinity for ligand, and the liganded or oxygenated relaxed (R) state, which exhibits high affinity for ligand. The degree of shift in the oxygen equilibrium curve (OEC) is reported as a decrease (left-shift) or increase (right-shift) in $P_{50}$ (oxygen tension at 50% Hb $O_2$ saturation). Only T-state Deoxy HbS can be incorporated into insoluble fibers, and thus, the kinetics of HbS polymerization and RBC sickling are favored primarily in hypoxic conditions. Hence, allosteric modulation compounds that not only destabilizes the T-state, but also stabilizes the $O_2$-liganded quaternary R-state promotes increased $O_2$ affinity, preventing HbS from forming insoluble fibers.[27-29,31-33]

Several aromatic aldehydes, e.g. Voxelotor,[26] INN-312, SAJ-310, TD-7, and 5-Hydroxymethylfurfural (HMF) and its derivatives[27-32,34-37] are known to have this allosteric and/or pharmacologic property by forming a Schiff-base covalent interaction with the N-terminal αVal1 nitrogens at the α-cleft of Hb that stabilize the R-state Hb and/or destabilize the T-state Hb, making them potential antisickling agents for the treatment of SCD. As noted above, Voxelotor is approved for the treatment of SCD, and although showed increased Hb levels and reduced hemolysis in SCD patients,[26] these surrogate end-points are not long-term clinical outcomes. However, the study provided encouraging evidence that Hb-binding agents may have disease-modifying potential. 5-HMF has also been studied in the clinic, and found to prevent hypoxia-induced RBC sickling, along with encouraging clinical outcomes, including reduction in pain. Unfortunately, significant and rapid metabolic oxidation of the aldehyde moiety resulting in poor pharmacokinetic (PK) properties (short half-life and suboptimal bioavailability) led to failure of the phase II clinical studies.[38-40] Other promising aromatic aldehyde antisickling compounds, e.g. vanillin and several of its derivatives, e.g. TD-7 or INN-312 also suffered similar poor PK outcomes. The thiazolidine complex of 5-HMF where the aldehyde is protected by L-cysteine extended 5-HMF half-life 2-fold in-vivo.[41] Unlike 5-HMF and Voxelotor that act exclusively via $O_2$-dependent mechanism to prevent hypoxia-induced RBC sickling, INN-312 exhibits both $O_2$-dependent and $O_2$-independent antisickling activities, the latter mechanism of action due to disruption of key intermolecular contacts necessary for stable polymer formation.[34,36] This novel dual mechanism of action has the potential to provide for even more potent anti-sickling effects with better clinical outcomes.

Several non-aromatic aldehyde compounds have also been studied for their antisickling potentials. These compounds, unlike aromatic aldehydes affect their antisickling activities by covalently binding to the surface-located βCys93 of Hb to destabilize the T-state Hb, resulting in increased Hb oxygen affinity.[42] These compounds are also expected to directly destabilize the polymer by virtue of binding to the surface of the Hb. An example of βCys93 binder is Ethacrynic acid (ECA).[42] However, the diuretic activity of ECA precludes its use as an oral therapeutic agent for the treatment of SCD.[42] Thiol derivatives that also bind to βCys93 are currently being studied to treat SCD.[43,44]

Although, significant progress has been made in developing compounds to treat SCD, there is still a pressing need to provide safer, less expensive, easily administered and more effective therapeutic agents to treat SCD patients, particularly agents that could mitigate vaso-occlusion, pain, and ameliorate organ damage. These agents, unlike aromatic aldehydes, must be resistant to oxidative metabolism, form more stable covalent adduct, and importantly prevent RBC sickling via both $O_2$-dependent and $O_2$-independent mechanisms of action.

SUMMARY

An aspect of the disclosure provides 5-HMF derivatives containing reactive centers that are metabolically stable and capable of forming stable covalent interactions with Hb. Unlike 5-HMF, the compounds described herein are non-aldehydes. In some embodiments, the compounds possess enhanced pharmacokinetic (PK) properties and exhibit both $O_2$-dependent and $O_2$-independent antisickling mechanisms of action.

Another aspect of the disclosure provides a pharmaceutical composition comprising a compound as described herein and a pharmaceutically acceptable carrier.

Another aspect of the disclosure provides a method of treating a hypoxia-associated disease or condition in a subject in need thereof, comprising administering to the subject a therapeutically effective amount of a compound as described herein. In some embodiments, the hypoxia-associated disease or condition is selected from the group consisting of acute respiratory distress syndrome (ARDS), hemorrhagic shock, traumatic shock, cardiac arrest, cardiogenic shock, traumatic brain injury, stroke, cancer, myocardial infarction, myocardial ischemia, and vaso-occlusive crisis.

Another aspect of the disclosure provides a method of treating sickle cell disease in a subject in need thereof, comprising administering to the subject a therapeutically effective amount of a compound as described herein. In some embodiments, the therapeutically effective amount of said compound is sufficient to inhibit red blood cell (RBC) sickling. In some embodiments, the compound is resistant to oxidative metabolism. In some embodiments, the inhibiting of said RBC sickling occurs via both $O_2$-dependent and $O_2$-independent mechanisms of actions.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

DETAILED DESCRIPTION

Figure 1:
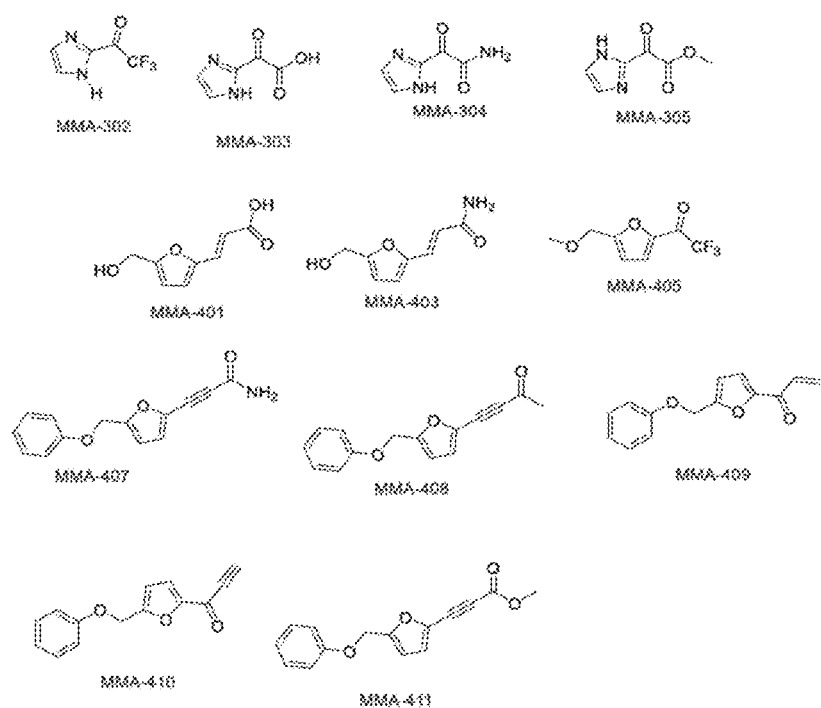
FIG. 1. Structures of exemplary metabolically stable 5-HMF derivatives according to some embodiments of the disclosure.

Embodiments of the disclosure provide 5-HMF derivative compounds that are useful for treating hypoxia-associated diseases or disorders. Without being bound by theory, unlike 5-HMF, the compounds of the present disclosure bind covalently with Hb through a Michael addition reaction with βCys93 to stabilize the R-state and/or destabilize the T-state Hb. In some embodiments, the compounds may also bind with N-terminal αVal1 at the α-cleft of the protein. This covalent binding to Hb stabilizes the relaxed state Hb and/or destabilizes the tense state Hb with a concomitant increase in the protein's affinity for oxygen to prevent hypoxia-related HbS polymerization and RBC sickling. These compounds, also by virtue of binding to βCys93, which is located on the surface of the molecule, can also exhibit an $O_2$-independent antisickling effect by directly destabilizing the polymer. Additionally, these compounds can exhibit several secondary pharmacologic effects, including prevention of oxidative stress, hemolysis, inflammation, vaso-occlusion, and increasing oxygenation of hypoxic tissues. The covalent binding nature, extended therapeutic duration of action because of resistance to metabolism, and the multiple therapeutic effects of these compounds also advantageously decrease the therapeutic dose required for efficacy, compared to 5-HMF.

The compounds disclosed herein comprise a metabolically stable reactive center which makes the compounds resistant to oxidative metabolism and allows formation of a covalent adduct interaction with a Hb protein, including HbS, with greater stability. In addition, the compounds may inhibit RBC sickling via both $O_2$-dependent and $O_2$-independent mechanisms.

In some embodiments, the compounds have the generic formula of Formula I:

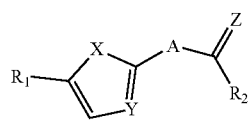

FORMULA I wherein X and Y are the same or different and are independently C, O, S, N or NH;

wherein Z is O, S or NR$_3$, where R$_3$ is H or a C$_{1-6}$ alkyl group;

wherein A is present or absent, and when A is present, A is selected from the group consisting of carbonyl, alkene between two carbons, and alkyne between two carbons;

wherein R$_2$ is selected from the group consisting of hydroxyl, amine, carboxylate, carboxylic acid, substituted or unsubstituted C$_{1-6}$ alkane, substituted or unsubstituted substituted or unsubstituted C$_{1-6}$ alkene, substituted or unsubstituted C$_{1-6}$ alkyne, substituted or unsubstituted C$_{1-6}$ alkyl halide, substituted or unsubstituted C$_{1-6}$ ether, and substituted or unsubstituted C$_{1-6}$ ester, wherein R$_1$ is any of
i) H, OH, CF$_3$, or NR$_6$R$_7$ where R$_6$ and R$_7$ are the same or different and are independently H or a C$_{1-6}$ alkyl group,
ii) substituted or unsubstituted alkyl, alkoxy, hydroxylalkyl, aryl or O-aryl, or
iii) a moiety having the following general formula:

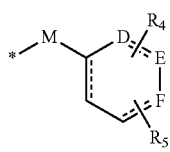

wherein R$_4$ and R$_5$ are the same or different and are independently H, OH, a halogen, a substituted or unsubstituted alkyl, a substituted or unsubstituted alkoxy, a substituted or unsubstituted hydroxyl-alkyl, a substituted or unsubstituted aryl, or a substituted or unsubstituted O-aryl;

wherein D, E and F are independently C or N (e.g., phenyl, pyridyls, and other heterocyclics);

M is a saturated or unsaturated bridging or linking chain of 1 to 10 atoms in length wherein at least some atoms or atomic groups in M are selected from the group consisting of C, CH$_2$, CO, O, S, NH, NHCO, NHCONH, and OCO, wherein the asterisk marks the point of attachment to the five membered ring of Formula 1, and wherein M is substituted or unsubstituted.

Exemplary substitutions of M included must are not limited to halogens, halogenated alkyls, amines, sulfyls, alkyls, esters, and ethers. M may be 2 to 8 atoms in length.

As used herein, any "R" group(s) such as, without limitation, R, R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, and so on represent substituents that can be attached to the indicated atom. An R group may be substituted or unsubstituted.

The term "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "C$_1$-C$_4$ alkyl" or similar designations. By way of example only, "C$_1$-C$_4$ alkyl" indicates that there are one to four carbon atoms in the alkyl chain, i.e., the alkyl chain is selected from methyl, ethyl, propyl, iso-propyl, n-butyl, isobutyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

The term "hydroxy alkyl" refers to a hydroxy derivative of an alkyl radical.

The term "alkenyl" refers to an alkyl group that contains in the straight or branched hydrocarbon chain one or more double bonds. An alkenyl group may be unsubstituted or substituted.

The term "alkynyl" refers to an alkyl group that contains in the straight or branched hydrocarbon chain one or more triple bonds. An alkynyl group may be unsubstituted or substituted.

The term "substituted" refers to, for example, an alkyl group substituted by, for example, about one, two three or four substituents, examples of which include but are not limited to: halo, hydroxy, alkoxy, oxo, alkanoyl, aryloxy, alkanoyloxy, amino, alkylamino, substituted alkylamino, cycloalkylamino, substituted cycloalkylamino, arylamino, substituted arylamino, aralkylamino, substituted aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. SO$_2$NH$_2$, substituted sulfonamido, nitro, cyano, carboxy, carbamyl, e.g. CONH$_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. These substituents may be further substituted, e.g. with alkyl, alkoxy, aryl, aralkyl, etc.

The term "alkoxyl" refers to a radical of —O-alkyl.

The term "alkyl halide" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amine" refers to nitrogen-containing groups, such as NH$_3$, NH$_2$, and NR$^1$R$^2$, wherein R$^1$ and R$^2$ can each be independently hydrogen, alkyl, substituted alkyl, aryl, substituted aryl, and aralkyl, alkylene, arylene, aralkylene. Thus, "amine" as used herein can refer to a primary amine, a secondary amine, or a tertiary amine.

The term "halogen" or "halo" refers to, e.g. fluorine, chlorine, bromine and iodine.

The term "aryl" refers to compounds which contain an aromatic group, e.g. a monocyclic or polycyclic aromatic compound. Monocyclic aryls generally have about 4 to about 7 carbon atoms, bicyclic aryls may have e.g. from about 7 to about 11 carbon atoms, and tricyclic aryls may contain from about 10 to about 15 or more carbon atoms. Exemplary aryls are or comprise groups that include but are not limited to: phenyl, naphthyl, biphenyl (diphenyl), thienyl, indolyl, etc. Aryls may be substituted or unsubstituted, and may or may not include one or more heteroatoms (e.g. S, N, etc.) in one or more ring structures (heteroaryls).

The term "arylalkyl" refers to an aryl or a substituted aryl group bonded directly to an alkyl group, such as benzyl.

The term "substituted aryl" refers to an aryl group substituted by, for example, about one to about four (e.g. 1, 2, 3, or 4) substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkylsulfonyl, sulfonamido, aryloxy and the like.

The substituent may be further substituted by hydroxy, halo, alkyl, alkoxy, alkenyl, alkynyl, aryl or aralkyl.

The term "carbonyl group" refers to a C=O group.

The term "carboxyl group" refers to a COOH group.

The term "cyano" group refers to a "—CN" group.

The terms "heterocycle" and "heterocyclic" refer to an optionally substituted, fully saturated or unsaturated, aromatic or nonaromatic cyclic group which, for example, is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

The term "heteroatoms" shall include at least oxygen, sulfur and nitrogen.

Exemplary compounds within the practice of the invention include but are not limited to

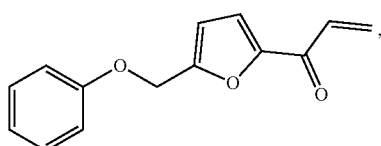

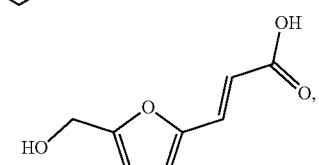

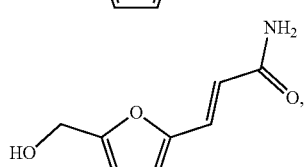

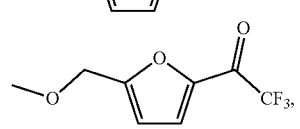

-continued

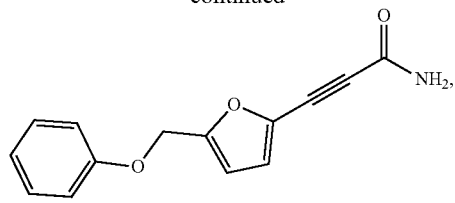

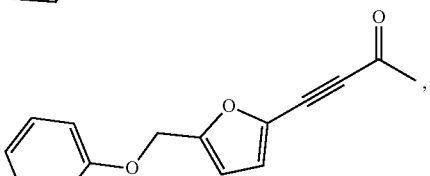

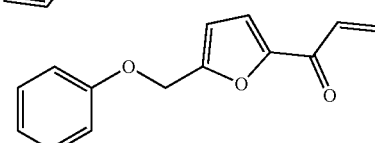

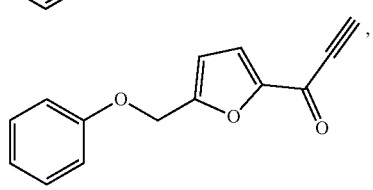

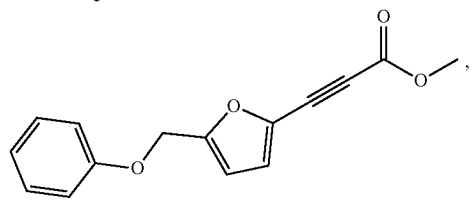

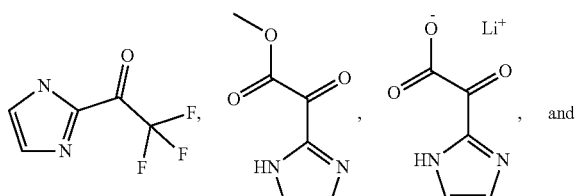

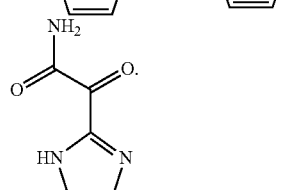

FIG. 1 present the structures of several exemplary compounds which can be used in the practice of the invention.

The compounds of the disclosure may form salts which are also within the scope of this disclosure. Pharmaceutically acceptable (i.e. non-toxic, physiologically acceptable) salts are preferred, although other salts are also useful, e.g., in isolating or purifying the compounds of this disclosure.

"Salts" or "pharmaceutically acceptable salts" refers to the relatively non-toxic, inorganic and organic acid addition salts, and base addition salts, of compounds of the present disclosure. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like A solvate is the result of solvation which is an interaction of a solute (i.e. compound of the disclosure) with a solvent. Solvation leads to stabilization of the solute species in the solution. A solvate refers to the solvated state, whereby an ion in a solution is surrounded or complexed by solvent molecules. Exemplary solvents include, but are not limited to, propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (Cremophor® EL, BASF Corp.), polyoxyethyleneglycerol oxystearate (Cremophor® RH 40 (polyethyleneglycol 40 hydrogenated castor oil) or Cremophor® RH 60 (polyethyleneglycol 60 hydrogenated castor oil), BASF Corp.) and the like); fractionated coconut oil (for example, mixed triglycerides with caprylic acid and capric acid (Miglyol® 812, available from Huls A G, Witten, Germany) and the like); Tween® 80; isopropyl palmitate; isopropyl myristate; pharmaceutically acceptable silicon fluids; and the like.

The compound may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type.

The compounds described herein are useful for the treatment of diseases that can be ameliorated by increasing Hb oxygen affinity, for example, SCD (which may also be referred to as "sickle cell anemia"), and hypoxia-underlying or associated diseases, e.g. hemorrhagic and traumatic shock, cardiac arrest and cardiogenic shock, traumatic brain injury, cancer, stroke, myocardial infarction, myocardial ischemia, vaso-occlusive crisis, etc. The treatment methods disclosed herein may include a step of diagnosing a subject with SCD or hypoxia-underlying diseases, e.g. hemorrhagic and traumatic shock, cardiac arrest and cardiogenic shock, traumatic brain injury, cancer, stroke, myocardial infarction, myocardial ischemia, vaso-occlusive crisis, etc. The compounds described herein can also be used to increase tissue oxygenation or as a means to hyperoxygenate tumors making them more susceptible to radiation therapy.

Exemplary methods of the invention can be used to treat any patient or subject suffering from or likely to suffer from a disease or condition which can be prevented, treated, cured, or ameliorated (i.e. disease symptoms are abated) by increasing oxygenation to hypoxic tissues. Various embodiments or scenarios of use of the methods of the invention include but are not limited to patients who have incurred an acute or chronic illness or injury in which the body has become hypoxic. The agents act to enhance oxygen delivery from hemoglobin to the hypoxic tissue.

The exemplary methods of the invention involve administering compositions comprising at least one (i.e. one or more) of the compounds disclosed herein to a patient in need thereof. The present disclosure thus also provides compositions which comprise the compounds as described herein, usually together with a pharmacologically suitable carrier or diluent. In some embodiments, one substantially purified compound is present in a composition; in other embodiments more than one compound is present, each compound being substantially purified prior to being mixed in the composition. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present disclosure may contain any such additional ingredients so as to provide the composition in a form suitable for administration. The final amount of compound in the formulations may vary. However, in general, the amount in the formulations will be from about 1% to about 99%.

The compound compositions (preparations) of the present disclosure may be administered by any of the many suitable means which are well known to those of skill in the art, including but not limited to: by injection, inhalation, orally, intravaginally, intranasally, by ingestion of a food or product containing the compound, topically, as eye drops, via sprays, etc. In exemplary embodiments, the mode of administration is orally or by injection. In addition, the compositions may be administered in conjunction with other treatment modalities which are used to treat SCD or other conditions associated with hypoxia, examples of which include but are not limited to the administration of hydroxyurea, L-glutamine (Endari), Crizanlizumab (Adakveo), Voxelotor (Oxbryta, aka GBT440), vanillin, supplemental oxygen, allosteric effectors of Hb, including those that increase the oxygen affinity of hemoglobin, e.g. 5-HMF, agents that decrease Hb affinity for oxygen, e.g. RSR13, etc.

The compositions of the present disclosure may also contain other components such as, but not limited to, additives, adjuvants, buffers, tonicity agents, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

Embodiments of the disclosure also include methods of preparing the compounds and compositions disclosed herein. Various suitable methods are known in the art.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the compound is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1, 5, 10, 20, 30, 40, 50, 60, 70, 80, 90, 100, 150, 200, 250, 300, 350, 400, 450, 500, 550, 600, 650, 700, 750, 800, 850, 900, 950, or 1000 mg of the compound, including all multiples of 5 and 10 between 0.01 and 1000 (e.g. 100, 105, 110, 115, etc.). An effective amount of the drug is ordinarily supplied at a dosage level from 0.0002 mg/kg to about 20 mg/kg of body weight per day, especially from about 0.001 mg/kg to 7 mg/kg of body weight per day.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1. Synthesis of Compounds

A. Materials and General Procedures

Melting point was performed using OPTIMELT® Automated Melting Point System Digital Image; Processing Technology SRS, Stanford Research Systems (Sunnyvale, Calif., USA); NMR spectroscopy was recorded on Bruker AVANCE® III 400 (Bruker, Fällanden, Switzerland); LCMS spectroscopy was performed on Agilent Technologies 1260 Infinity LC/MSD system with DAD¥ELSD Alltech 3300 and Agilent; LC¥MSD G6120B mass-spectrometer (Santa Clara, Calif., USA); High-resolution mass spectroscopy (HRMS) was performed by separation and mass spectrometric detection techniques and were performed with an Infinity 1260 UHPLC system (Agilent Technologies, Waldbronn, Germany) coupled to an 6224 Accurate Mass TOF LC/MS system (Agilent Technologies, Singapore). Chromatographic separation was achieved using Agilent ZORBAX® C18 column (100 mm x 2.1 mm, 1.9 μm particle size). Mobile phase A consisted of 0.1% formic acid in water and mobile phase B consisted of 0.1% formic in acetonitrile. Injection volume of the samples solutions was 1 μL. Separation was performed at a constant flow rate of 0.4 ml/min at 40° C. A linear gradient started at 5% mobile phase B and ramped to 95% in 6.5 min, flushed 1.5 minute at 95% B. The column was re-equilibrated for 2 min. with 5% mobile phase A. Positive ion mass spectra of the column eluate were recorded in the range of m/z 100-1500 at a measuring frequency of 9500 transients/s and a detection frequency of 4 GHz. The Agilent ion source was operated using the following conditions: pressure of nebulizing gas (N2) was 40 psi; temperature and flow rate of drying gas (N2) was 320° C. and 6 l/min, respectively; the capillary voltage was set to 4 kV, the fragmentor potential to 120V and the skimmer potential to 75V. Solvents and chemicals were HPLC grade. Water was purified by Millipore Water Purification System. All the chemicals, reagents and solvents had been purified and/or dried according to well-known literature methods; vendors' names: UORSY and Enamine (Kiev, Ukraine).

B. Synthesis of MMA-301, MMA-302, MMA-303, MMA-304 and MMA-305

Preparation of (E)-4-(1H-imidazol-2-yl)but-3-en-2-one (MMA-301)

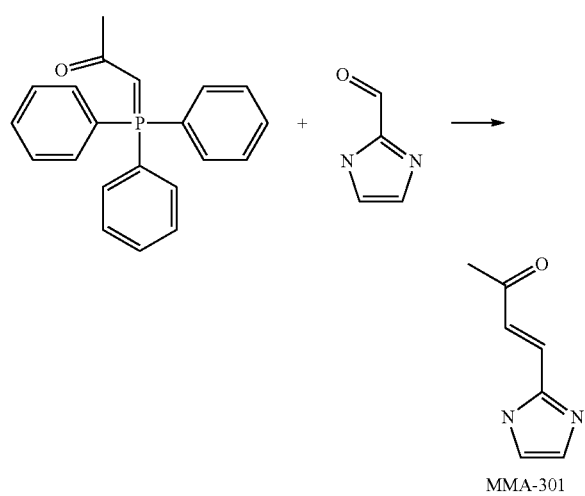

1-(triphenyl-$\lambda^5$-phosphanylidene)propan-2-one (3.64 g, 11 mmol) and 1H-imidazole-2-carbaldehyde (1 g, 10 mmol) was subsequently added to THF (150 mL) and the resulting suspension was stirred for 9 h. Then the reaction mixture was evaporated of the solvents and put on column chromatography to obtain solid residue results in target compound MMA-301 (0.136 g, 10% yield) as beige solid. $^1$H NMR (400 MHz, DMSO-$d_6$) δ 12.72 (s, 1H), 7.35 (d, J=16.4 Hz, 1H), 7.25 (s, 2H), 6.76 (d, J=16.4 Hz, 1H), 2.31 (s, 3H); $^{13}$C NMR (126 MHz, DMSO-$d_6$) δ 198.25, 149.04; 143.41, 131.84, 127.06, 27.66; LC-MS (ESI), RT=0.271 min, m/z 137.20 [M+H]$^+$; HRMS (ESI), RT=0.563 min, m/z 137.0713 [M+H]$^+$, formula $C_7H_8N_2O$.

Preparation of 2,2,2-trifluoro-1-(1H-imidazol-2-yl)ethan-1-one (MMA-302)

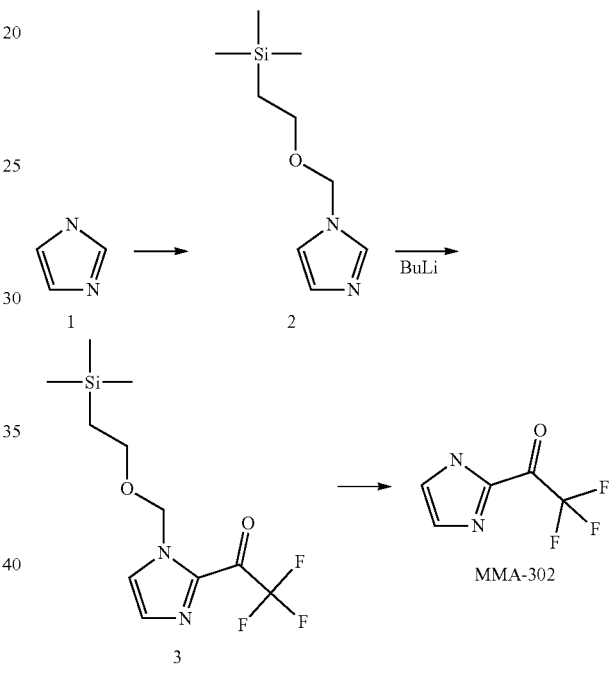

To sodium hydride (1.4 g, 35 mmol, 60% dispersion in mineral oil) in THF (20 mL) which was cooled to 0° C. over a period of 10 minutes, was slowly added imidazole (2 g, 29.4 mmol) in THF (50 mL) under Ar atmosphere. The resulting mixture was stirred at room temperature (r.t.) for 30 minutes, and then to it was added slowly (2-(chloromethoxy)ethyl)trimethylsilane (5.4 g, 32.4 mmol) at 0° C. under Ar atmosphere. The mixture was warmed to r.t. and stirred for 14 hours. Then the reaction mixture was concentrated in vacuo and diluted with EtOAc (200 mL), and washed with water (3x50 mL). The organic layer was dried over $Na_2SO_4$, filtered and evaporated to afford crude product 1-((2-(trimethylsilyl)ethoxy)methyl)-1H-imidazole (4.9 g 85%), which used without further purification.

To a stirred solution of compound 1-((2-(trimethylsilyl)ethoxy)methyl)-1H-imidazole (4 g, 1.56 mmol) and N,N,N',N'-tetramethyl ethylenediamine (3.52 g 30.26 mmol 0.35 mL, 2.35 mmol) in THF (80 mL) cooled to -78° C. was added—butyllithium (1.6M solution in THF) (12.1 mL, 30.26 mmol) dropwise. The solution was stirred at -78° C. for 45 min then ethyl trifluoroacetate (5.73 g, 40.34 mmol) was added dropwise. The solution was stirred for an additional at -78° C. for 2 h. The reaction mixture was quenched by the addition of water and warmed to r.t. and extracted with EtOAc (3×150 mL). The combined organic layers were dried over $Na_2SO_4$, filtered and concentrated to dryness in vacuo to give product 2,2,2-trifluoro-1-(1-((2-(trimethylsilyl)ethoxy)methyl)-1H-imidazol-2-yl)ethan-1-one (5.05 g, 85%), which used without further purification.

To a solution of 2,2,2-trifluoro-1-(1-((2-(trimethylsilyl)ethoxy)methyl)-1H-imidazol-2-yl)ethan-1-one (1 g, 3.4 mmol) in DCM (5 mL) was added TFA (5 mL) and the mixture was stirred at r.t. for 10 h. The reaction mixture was concentrated in vacuo. The solid was dissolved in EtOAc and solution was washed with sat. $NaHCO_3$ (2×15 mL). Organic layer was washed with brine (10 mL), dried over $Na_2SO_4$, filtered, and concentrated in vacuo to give crude target material (0.7 g). The crude material was recrystallized from EtOAc/Hex mixture (1/1) resulting of MMA-302 (0.5 g, 89% yield). Melting point 79.6° C.; $^{13}C$ NMR (126 MHz, DMSO-$d_6$) δ 157.42, 131.73, 89.63, 81.85, 80.18, 77.32, 76.07, 54.41, 45.94, 39.25, 30.90; $^1H$ NMR (400 MHz, DMSO-$d_6$) δ 14.22 (s, 1H), 7.62 (d, J=135.9 Hz, 2H); LC-MS (ESI), RT=0.233 min, m/z 165 [M+H]$^+$; HRMS (ESI), RT=0.423 min, m/z 165.0280 [M+H]$^+$, formula $C_5H_3F_3N_2O_2$.

Preparations of MMA-303, MMA-304 and MMA-305

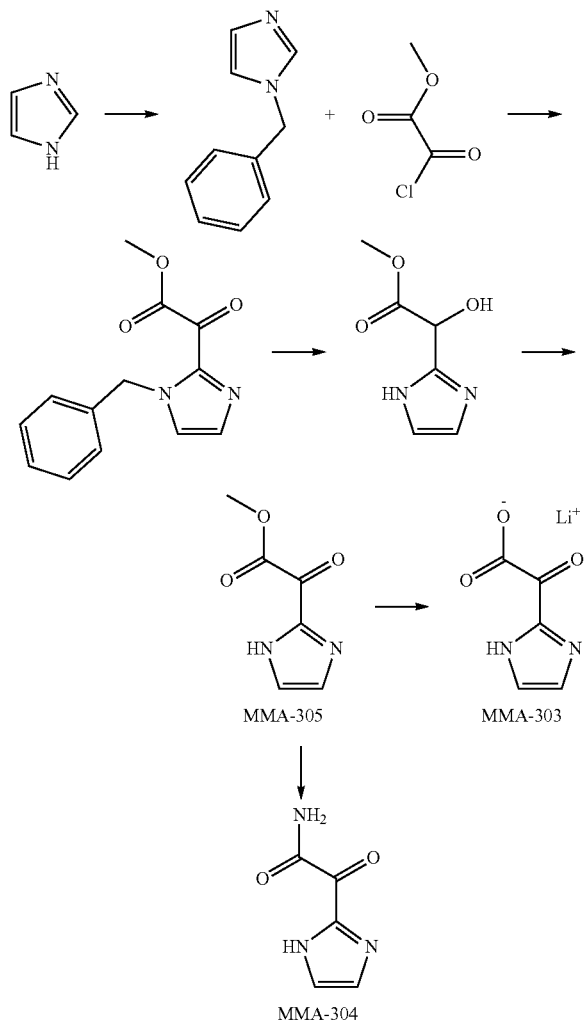

To a solution of benzyl bromide (0.365 g, 2.132 mmol) in acetonitrile (15 ml) was added potassium carbonate (0.589 g, 4.265 mmol) followed by imidazole (0.290 g, 4.265 mmol). The resulting mixture was refluxed for 30 min, then it was cooled to rt, filtered and filtrate was evaporated. The residue was dissolved in DCM (25 mL), washed with aq. $Na_2CO_3$ (10 mL), brine (10 mL), dried over $Na_2SO_4$ and evaporated to dryness to give 1-benzyl-1H-imidazole (0.303 g, 90% yield) as a beige crystal for use without further purification. Methyl 2-chloro-2-oxoacetate (0.235 g, 1.918 mL) was added dropwise over 20 min to a stirred solution of 1-benzyl-1H-imidazole (0.303 g, 1.918 mmol) in DCM (25 mL) at −20° C. Then DIPEA (0.247 g, 1.918 mmol) was added and the mixture was allowed to warm to r.t. The reaction mixture was stirred for an additional 12 h and then washed with $H_2O$ (3×20 mL). The organic layer was dried ($Na_2SO_4$) and evaporated under vacuum to give methyl 2-(1-benzyl-1H-imidazol-2-yl)-2-oxoacetate (0.412 g, 88% yield) as a brownish crystal.

To a solution of compound methyl 2-(1-benzyl-1H-imidazol-2-yl)-2-oxoacetate (0.412 g, 1.688 mmol) in methanol (15 mL) in three-necked round-bottomed flask was added palladium, 10% on carbon (0.041 g, 10% by weight). The reaction flask was evacuated and backfilled with hydrogen and the mixture was left to stir for 10 h. Then the reaction mixture was filtrated through a thin pad of silica gel followed by concentration and drying under vacuum afforded compound methyl 2-hydroxy-2-(1H-imidazol-2-yl)acetate (0.224 g, 85% yield) as an off-white solid. To a solution of compound methyl 2-hydroxy-2-(1H-imidazol-2-yl)acetate (0.224 g, 1.436 mmol) in $CHCl_3$ (25 mL) was added $MnO_2$ (1.25 g, 14.36 mmol) and the resulting mixture was left to stir for 10 h at 60° C. The resulting mixture was filtered through a thin pad of $SiO_2$, washed 2 times with MTBE and evaporated to dryness to give compound methyl 2-(1H-imidazol-2-yl)-2-oxoacetate (MMA-305) (161 mg, 73% yield) as a white solid. $^1H$ NMR (400 MHz, DMSO-$d_6$) δ 13.98 (s, 1H), 7.70 (s, 1H), 7.36 (s, 1H), 3.89 (s, 3H); $^{13}C$ NMR (126 MHz, Chloroform-d) δ 172.90, 162.78, 142.14, 53.36. LC-MS (ESI), RT=0.161 min, m/z 155.20 [M+H]$^+$; HRMS (ESI), RT=0.422 min, m/z 155.0448 [M+H]$^+$, formula $C_6H_6N_2O_3$.

To a solution of compound methyl 2-(1H-imidazol-2-yl)-2-oxoacetate (161 mg, 1.045 mmol) in MeOH (10 mL) was added lithium hydroxide monohydrate (43.87 mg, 1.045 mmol). After stirring for 1 h it was evaporated to dryness, re-evaporated with water, dried under high vacuum (0.3 mbar) to give MMA-303 (150 mg, 98% yield) as a light-yellow solid. $^1H$ NMR (400 MHz, DMSO-$d_6$) δ 13.07 (s, 1H), 7.21 (s, 2H); $^{13}C$ NMR (126 MHz, DMSO-$d_6$) δ 185.58, 167.56, 144.79, 133.64. LC-MS (ESI), RT=0.140 min, m/z 139.0 [M+H]$^+$; HRMS (ESI), RT=0.412 min, m/z 139.0148 [M−H]$^+$, formula $C_5H_3N_2O_3$.

To a solution of MMA-305 (0.161 g, 1.045 mmol) in MeOH (10 mL) was added NH3 (saturated solution in methanol, 15 mL) and the resulting mixture was left to stir overnight at 55° C. The resulting mixture was filtered, the filter cake was washed 2 times with MTBE and dried to give MMA-304 (121 mg, 83% yield) as an off-white solid; $^1H$ NMR (400 MHz, DMSO-$d_6$) δ 8.55 (s, 1H), 7.91 (s, 1H), 7.39 (s, 2H); $^{13}C$ NMR (126 MHz, Chloroform-d) δ 179.46, 166.33, 143.94, 128.43 (2C); LC-MS (ESI), RT=0.148 min, m/z 140.00 [M+H]$^+$; HRMS (ESI), RT=0.411 min, m/z 140.0458 [M+H]$^+$, formula $C_5H_5N_3O_2$.

C. Synthesis of MMA-401, MMA-402, MMA-403, MMA-404 and MMA-406

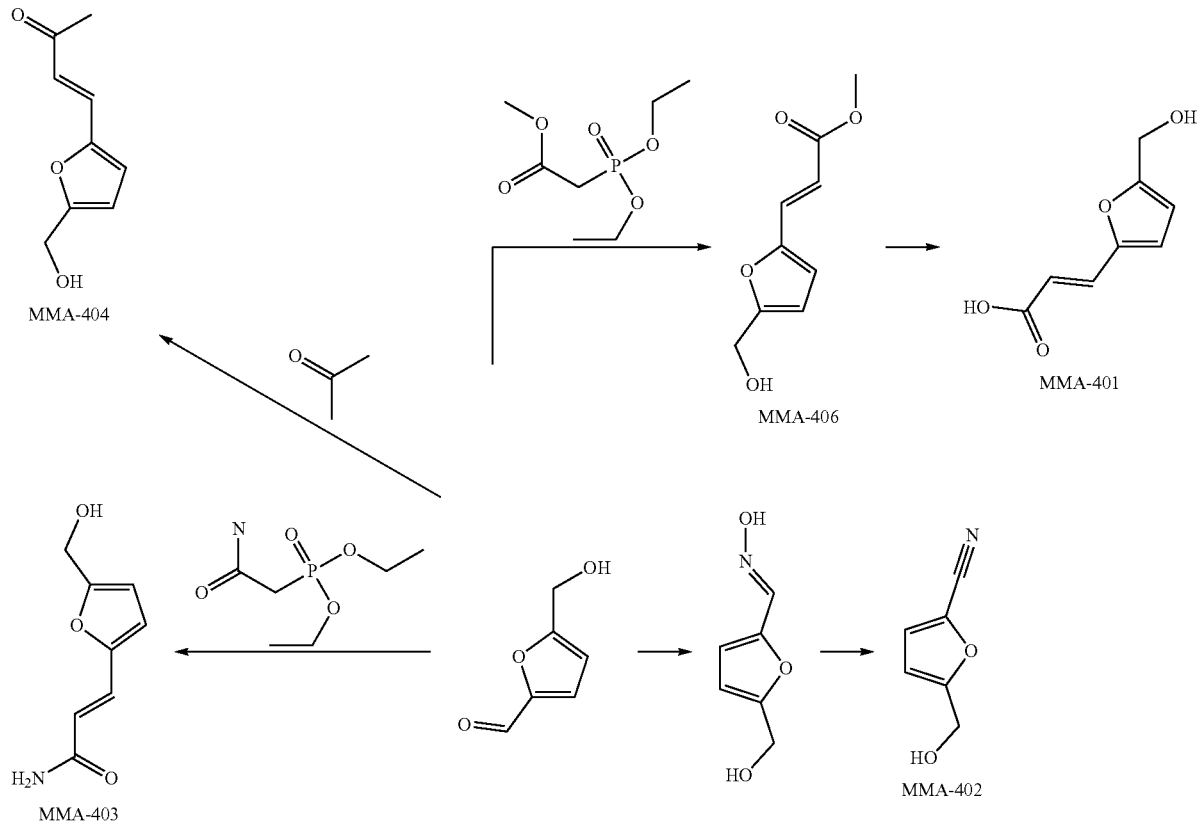

A mixture of methyl 2-(diethyl phosphono)acetate (5 mmol, 1.05 g), potassium carbonate (12 mmol, 1.63 g), methanol (25 mL) and 5-(hydroxymethyl)furan-2-carbaldehyde (4 mmol, 0.504 g) was heated at 70° C. under Ar atmosphere for 10 min. The mixture was cooled, filtered, the solvent evaporated under reduced pressure. The residue was purified by column chromatography (hexane-EtOAc, 1:1) to give methyl (E)-3-(5-(hydroxymethyl)furan-2-yl)acrylate (MMA-406) (0.64 g, 88% yield). Melting point 66° C.; $^1$H NMR (500 MHz, Chloroform-d) δ 7.39 (d, J=15.8 Hz, 1H), 6.56 (d, J=3.5 Hz, 1H), 6.37 (d, J=3.4 Hz, 1H), 6.30 (d, J=15.8 Hz, 1H), 4.65 (s, 2H), 3.78 (s, 3H), 2.13 (s, 1H); $^{13}$C NMR (126 MHz, Chloroform-d) δ 167.54, 156.55, 150.73, 131.08, 115.74, 115.40, 110.20, 57.60, 51.70. The mixture of methyl (E)-3-(5-(hydroxymethyl)furan-2-yl)acrylate (0.64 g) and LiOH (0.43 g, 3 eq.) in THF—H$_2$O (7:3, 10 ml) was stirred for 7 h at RT and then MTBE (10 mL) was added. The aqueous layer was separated and acidified with aq 4 M HCl. Subsequently, the aqueous layer was extracted with EtOAc (3×10 mL). The combined organic layers were washed with Brine (2×10 mL) solution and dried (anhydrous Na$_2$SO$_4$), filtered, and evaporated to dryness under reduced pressure to afford (E)-3-(5-(hydroxymethyl)furan-2-yl)acrylic acid (MMA-401) (0.35 g, 60% yield). Melting point 138° C.; $^1$H NMR (400 MHz, DMSO-d$_6$) δ 12.33 (s, 1H), 7.35 (d, J=15.7 Hz, 1H), 6.85 (d, J=3.3 Hz, 1H), 6.43 (d, J=3.3 Hz, 1H), 6.10 (d, J=15.7 Hz, 1H), 5.36 (t, J=5.9 Hz, 1H), 4.42 (d, J=5.4 Hz, 2H); $^{13}$C NMR (126 MHz, Chloroform-d) δ 169.08, 157.41, 150.48, 131.26, 115.90, 115.54, 109.77, 57.15, 40.62-39.26 (m); HRMS (ESI), RT=0.790 min, m/z 167.0350 [M−H]$^-$, formula C$_8$H$_8$O$_4$.

5-(hydroxymethyl)furan-2-carbaldehyde (0.5 g, 3.9 mmol) in 50 mL EtOH and hydroxylamine hydrochloride (0.505 g, 7.1 mmol) in H$_2$O (5 mL). The mixture was boiled during 20 minutes. The reaction mixture cooled and quenched with HCl (10%) to neutral reaction. The organic phase is extracted CH$_2$Cl$_2$ (2×20 mL), combined, dried over Na$_2$SO$_4$ and concentrated in vacuo to give (E)-5-(hydroxymethyl)furan-2-carbaldehyde oxime (0.297 g, 2.1 mmol, 53.84% yield). 4 mL of Et$_3$N was added to solution of (E)-5-(hydroxymethyl)furan-2-carbaldehyde oxime (564 mg, 4 mmol) in 20 mL THF. To this mixture was added dropwise TFAA (2 mL) at 0° C. and stirred at rt for 12 h. Then the reaction mixture quenched with saturated aq. solution of NaHCO$_3$, stilled for 30 minutes, extracted with DCM (3×20 mL); organic layers was combined, washed with 5% HCl (20 mL), water (2×15 mL), brine (10 mL), concentrated in vacuo and purified by column chromatography to give target compound 5-(hydroxymethyl)furan-2-carbonitrile (MMA-402) 0.186 mg, 95+% purity, 37.8% yield. $^1$H NMR (400 MHz, DMSO-d$_6$) δ 7.49 (d, J=3.6 Hz, 1H), 6.56 (d, J=3.6 Hz, 1H), 5.35 (d, J=12.2 Hz, 1H), 4.47 (s, 2H). $^{13}$C NMR (126 MHz, DMSO-d$_6$) δ 162.33, 124.89, 124.22, 112.40, 109.24, 56.06; HRMS (ESI), RT=2.075, m/z 124.0392 [M+H]$^+$, formula C$_6$H$_5$NO$_2$.

To a suspension of LiCl (0.2 g, 1 eq) in dry MeCN (20 mL) was added 5-(hydroxymethyl)furan-2-carbaldehyde (0.84 g, 4 mmol, 1 eq) and DBU (0.6 mL, 1 eq). The mixture was stirred for 10 min at ambient temperature before compound 2 (0.5 g, 4 mmol, in dry CHCl$_3$) was added. The reaction was monitored via TLC and quenched with sat. NH$_4$Cl after complete conversion. Then the aqueous layer was extracted with EtOAc (3×25 mL), next combined organic layers were washed with water (2×15 mL) and brine (10 mL), dried over Na$_2$SO$_4$, evaporated in vacuo and purified by column chromatography (on silica gel eluting with DCM/hexane (from 50/50)) to give (E)-3-(5-(hydroxymethyl)furan-2-yl)acrylamide (MMA-403) (0.36 g, 2 mmol, 46% yield); Melting point 131-156° C.; $^1$H NMR (400 MHz, DMSO-d$_6$) δ 7.53 (s, 1H), 7.17 (d, J=15.7 Hz, 1H), 7.04 (s, 1H), 6.67 (d, J=3.4 Hz, 1H), 6.36 (d, J=15.2 Hz, 2H), 5.30 (t, J=5.6 Hz, 1H), 4.41 (d, J=5.8 Hz, 2H); $^{13}$C NMR (101 MHz, DMSO-d$_6$) δ 166.98, 157.76, 150.70, 127.08, 119.49, 115.10, 109.90, 56.27; HRMS (ESI), RT=1.909 min, m/z 168.0654 [M+H]$^+$, formula C$_8$H$_9$NO$_3$.

To a stirred solution of 5-(hydroxymethyl)furan-2-carbaldehyde (0.5 g, 4.0 mmol) in EtOH (20 mL) and acetone (0.5 g, 8.6 mmol), at r.t. under Ar, was added dropwise 10% aq NaOH (3.2 mL). The mixture was stirred at r.t. for 14 h. Then solvent was removed in vacuo. The residue was dissolved in CH$_2$Cl$_2$ (50 mL) and washed with 5% aq HCl (2×25 mL) and then with H$_2$O (n×20 mL) until neutral. Organic extract was dried (Na$_2$SO$_4$) and concentrated in vacuo. The residue was purified by column chromatography (hexane-EtOAc, 1:3 to give (E)-4-(5-(hydroxymethyl)furan-2-yl)but-3-en-2-one (MMA-404) (0.3 g, 46% yield). Melting point 20° C.; $^1$H NMR (500 MHz, Chloroform-d) δ 7.33-7.16 (m, 1H), 6.70-6.52 (m, 2H), 6.40 (d, J=3.3 Hz, 1H), 4.65 (t, J=6.7, 2.9 Hz, 2H), 2.32 (s, 3H); $^{13}$C NMR (126 MHz, Chloroform-d) δ 197.95, 156.94, 150.71, 129.32, 124.08, 116.68, 110.42, 57.57, 27.97; HRMS (ESI), RT=3.895 min, m/z 167.0695 [M+H]$^+$, formula C$_9$H$_{10}$O$_3$.

D. Preparation of 2,2,2-trifluoro-1-(5-(methoxymethyl)furan-2-yl)ethan-1-one (MMA-405)

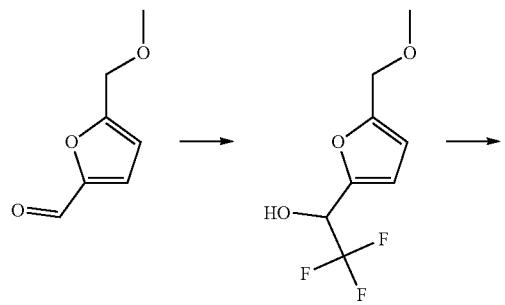

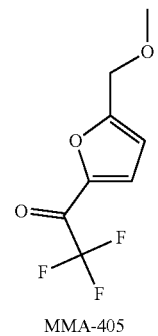

MMA-405

TBAF (15 mmol, 15 mL 1M solution in THF) was added to a mixture of 5-(methoxymethyl)furan-2-carbaldehyde (10 mmol, 1.4 g) at 0° C., followed by TMS-CF$_3$ (20 mmol, 1.7 g) in THF (15 mL) and resulting mixture was stirred at room temperature for 12 h. H$_2$O was added to reaction mixture and the aqueous layer was extracted with EtOAc (3×20 mL). Organic layers were combined, washed with brine (2×10 mL), dried over Na$_2$SO$_4$, filtered and concentrated in vacuo to give 2,2,2-trifluoro-1-(5-(methoxymethyl)furan-2-yl)ethan-1-ol (1.5 g, 71%).

To a solution of 2,2,2-trifluoro-1-(5-(methoxymethyl)furan-2-yl)ethan-1-ol (0.71 mmol, 0.15 g) in anhydrous EtOAc (15 mL) was added IBX (2-Iodoxybenzoic acid) (1.42 mmol, 0.4 g). The mixture was refluxed for 10 h. The mixture was cooled, then filtered and the solvent was concentrated in vacuo to give the product MMA-405 which was recrystallized from hexanes (0.13 g, 87% yield). $^1$H NMR (400 MHz, Chloroform-d) δ 7.47 (s, 1H), 6.58 (d, J=3.7 Hz, 1H), 4.51 (s, 2H), 3.43 (s, 3H); $^{13}$C NMR (126 MHz, Chloroform-d) δ 184.43, 165.08, 164.35, 132.64, 125.47, 114.25, 55.65, 52.66.

E. Preparation of MMA-407, MMA-408, MMA-409, MMA-410 and MMA-411

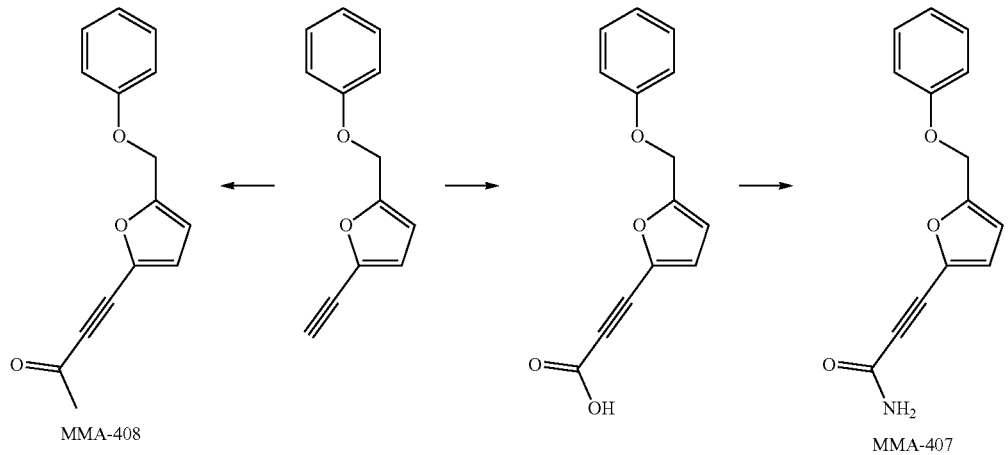

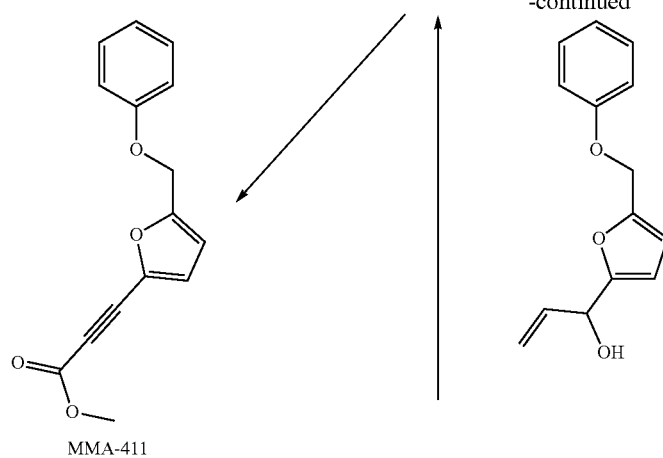
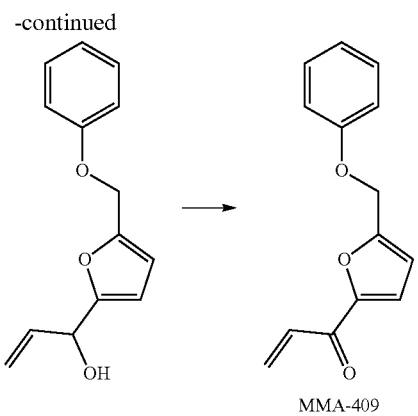

MMA-411

MMA-409

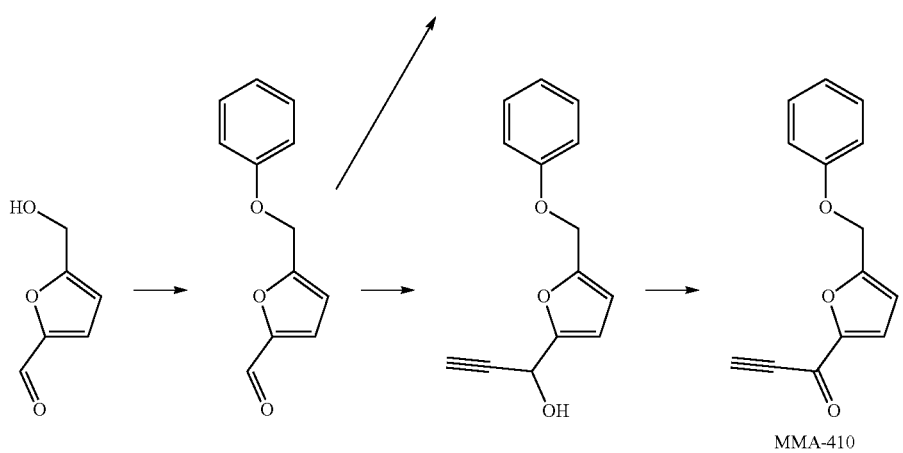

MMA-410

DIAD (5.29 g, 0.0262 mol) was added dropwise under Ar atmosphere to solution of 5-hydroxymethylfurfural 1 (3 g, 0.0238 mol), Ph$_3$P (6.89 g, 0.0262 mol) and phenol (2.46 g, 0.0262 mol) in THF (20 mL), which was cooled with ice. After adding, reacting mixture was warmed to ambient temperature and stirred for 3 h under inert atmosphere. Resulting solution was evaporated and purified by column chromatography (Hex:EtOAc=4:1) to give 16 g of 5-(phenoxymethyl)furan-2-carbaldehyde (yield=33.2%) as an orange solid.

K$_2$CO$_3$ (1.05 g, 7.2 mmol) was added to solution of 5-(phenoxymethyl)furan-2-carbaldehyde (1 g, 4.8 mmol) in dry methanol (10 mL) which was cooled with ice. Then solution of dimethyl-1-diazo-2-oxopropylphosphonate (1.12 g, 5.94 mmol) in methanol (10 mL) was added dropwise to resulting solution and stirred at r.t. for 11 h. Next reaction mixture was evaporated, organic layer was separated, washed with brine (10 mL), dried over Na$_2$SO$_4$ and evaporated to give crude 2-ethynyl-5-(phenoxymethyl)furan (1 g, yield=94%), which then was used without further purification.

To a solution of 2-ethynyl-5-(phenoxymethyl)furan (1 g, 5.05 mmol) in dry THF at −80° C. was added dropwise 2.5M solution of BuLi in hexane (2.1 ml, 5.55 mol). Resulted solution was stirred for 30 min. at −80° C. The reaction flask was evacuated and filled with hydrogen dry CO$_2$ left to stir for 1 h, and then slowly warmed to r.t. After 30 min, mixture was quenched by NH$_4$Cl solution and extracted with EtOAc (20 mL×3). Organic layers were combined, washed with water (10 mL×2) and brine (10 mL), dried over Na$_2$SO$_4$ and evaporated in vacuo to give crude 1 g of crude 3-(5-(phenoxymethyl)furan-2-yl)propiolic acid, which then was used without purification.

Ethyl chloroformate (0.497 g, 4.54 mol) was added at −15° C.-10° C. to solution of 3-(5-(phenoxymethyl)furan-2-yl)propiolic acid (1 g, 4.1 mmol) and Et$_3$N (0.46 g, 4.54 mol) in THF (10 mL). Resulted solution was stirred for 1 h. Then, 3 mL of 25% aqueous ammonia was added to reaction mixture and stirred for 1 h. Resulted mixture was diluted with EtOAc and washed 3 times with water (10 mL), then organic layer was separated, dried over Na$_2$SO$_4$ and concentrated in vacuum. After column chromatography (Hex:EtOAc=1:1) 3-(5-(phenoxymethyl)furan-2-yl)propiolamide (MMA-407) was obtained as an white solid (0.21 g, 0.57 mmol). Yield: 21.2% $^1$H NMR (400 MHz, DMSO-d$_6$) δ 8.25 (s, 1H), 7.77 (s, 1H), 7.31 (t, J=7.9 Hz, 2H), 7.07 (d, J=3.5 Hz, 1H), 7.02 (d, J=8.1 Hz, 2H), 6.97 (t, J=7.3 Hz, 1H), 6.74 (d, J=3.5 Hz, 1H), 5.10 (s, 2H). LC-MS (ESI), RT=1.210 min, m/z 242.0 [M+H]$^+$; HRMS (ESI), RT=0.790 min, m/z 242.0821 [M+H]$^+$, formula C$_{14}$H$_{11}$NO$_3$.

To a solution of 2-ethynyl-5-(phenoxymethyl)furan (1 g, 5.05 mmol) in dry THF at −80° C. was added dropwise 2.5M solution of BuLi in hexane (2.1 ml, 5.55 mol). Resulted solution was stirred for 30 min. at −80° C. The reaction flask was evacuated and filled with hydrogen dry CO$_2$ left to stir for 1 h, and then slowly warmed to r.t. After 30 min, mixture was quenched by NH$_4$Cl solution and extracted with EtOAc (20 mL×3). Organic layers were combined, washed with water (10 mL×2) and brine (10 mL), dried over Na$_2$SO$_4$ and concentrated in vacuum to give crude 1 g of crude 4-(5-

(phenoxymethyl)furan-2-yl)but-3-yn-2-one (MMA-408). After column chromatography (Hex:EtOAc=7:1) MMA-408 was obtained as an yellow solid (0.48 g, 2 mmol). Yield: 26.5%; $^1$H NMR (400 MHz, DMSO-$d_6$) δ 7.34-7.26 (m, 3H), 7.03 (d, J=8.0 Hz, 2H), 6.97 (t, J=7.3 Hz, 1H), 6.80 (d, J=3.7 Hz, 1H), 5.13 (s, 2H), 2.43 (s, 3H). $^{13}$C NMR (126 MHz, Chloroform-d) δ 155.77, 130.03, 123.75, 121.70, 115.21, 112.92, 61.82, 32.62. LC-MS (ESI), RT=1.425 min, m/z 241.2 [M+H]$^+$; HRMS (ESI), RT=6.547 min, m/z 241.0862 [M+H]$^+$, formula $C_{15}H_{12}O_3$.

Diisopropyl azodicarboxylate (DIAD) (5.29 g, 0.0262 mol) was added dropwise to solution of 5-hydroxymethyl-furfural (3 g, 0.0238 mol), Ph3P (6.89 g, 0.0262 mol) and phenol (2.46 g, 0.0262 mol) in THF (20 mL) under Ar atmosphere and cooled with ice. Then reacting mixture was warmed to ambient temperature and stirred 3 hours under inert atmosphere. Resulting solution was evaporated and purified by column chromatography (Hex:EtOAc=4:1) to give 1.6 g of 5-(phenoxymethyl)furan-2-carbaldehyde (yield=33.2%) as an orange solid To a solution of 5-(phenoxymethyl)furan-2-carbaldehyde (1 g, 4.95 mmol) in THF (10 mL) at 0° C. was added vinylmagnesium bromide (7.45 mL of 1N solution, 7.42 mmol) and stirred at ambient temperature for 10 h. Then, mixture was poured to EtOAc, washed with $H_2O$ (15 mL×2), dried over $Na_2SO_4$, evaporated to obtain 0.95 g of crude 1-(5-(phenoxymethyl)furan-2-yl)prop-2-en-1-ol (yield=83%).

2-Iodoxybenzoic acid (2.31 g, 8.26 mmol) was added to solution of 1-(5-(phenoxymethyl)furan-2-yl)prop-2-en-1-ol (0.95 g, 4.13 mmol) in dry EtOAc (20 mL). Resulted suspension was refluxed for 10 h. Then, it was cooled, filtrated and filtrate was evaporated to give crude product. MMA-409 was obtained as an yellow solid (0.164 g, 0.71 mmol) after column chromatography (Hex:EtOAc=4:1). Yield=17.4%. $^1$H NMR (400 MHz, DMSO-$d_6$) δ 7.68 (d, J=3.6 Hz, 1H), 7.31 (t, J=8.0 Hz, 2H), 7.22 (dd, J=17.0, 10.4 Hz, 1H), 7.05 (d, J=8.1 Hz, 2H), 6.98 (t, J=7.3 Hz, 1H), 6.85 (d, J=3.6 Hz, 1H), 6.39 (dd, J=17.1, 1.8 Hz, 1H), 5.94 (dd, J=10.4, 1.8 Hz, 1H). $^{13}$C NMR (126 MHz, Chloroform-d) δ 132.12, 130.04, 129.90, 121.72, 121.28, 115.21, 113.10, 62.05. LC-MS (ESI), RT=1.33 min, m/z 229.0 [M+H]$^+$; HRMS (ESI), RT=6.132 min, m/z 229.0869 [M+H]$^+$, formula $C_{14}H_{12}O_3$. To a solution of 5-(phenoxymethyl)furan-2-carbaldehyde (1 g, 4.95 mmol) in THF (15 mL) at 0° C. was added ethynylmagnesium bromide (14 ml of 0.5N solution, 7.42 mmol) and left to stir at ambient temperature for 10 h. Then, mixture was poured to EtOAc (20 mL), washed with $H_2O$ (15 mL×2), dried over $Na_2SO_4$, evaporated in vacuo to obtain 0.91 g of crude 1-(5-(phenoxymethyl)furan-2-yl)prop-2-yn-1-ol (yield=81%) for use without further purification.

2-Iodoxybenzoic acid (2.23 g, 7.98 mmol) was added to solution of 1-(5-(phenoxymethyl)furan-2-yl)prop-2-yn-1-ol (0.91 g, 3.99 mmol) in dry EtOAc (20 mL). Resulted suspension was refluxed for 11 h. Then, it was cooled, filtrated and filtrate was evaporated to give crude product. After column chromatography (Hex:EtOAc=4:1), MMA-410 was obtained as an yellow solid (0.398 g, 1.76 mmol). Yield=44.2%. $^1$H NMR (400 MHz, DMSO-$d_6$) δ 7.58 (d, J=3.7 Hz, 1H), 7.36-7.25 (m, 2H), 7.04 (d, J=8.0 Hz, 2H), 6.98 (t, J=7.3 Hz, 1H), 6.88 (d, J=3.7 Hz, 1H), 5.20 (s, 2H), 4.99 (s, 1H). $^{13}$C NMR (126 MHz, DMSO-$d_6$) δ 163.56, 158.06, 157.82, 154.24, 130.05, 124.10, 121.79, 115.21, 113.57, 84.36, 80.20, 62.00. LC-MS (ESI), RT=1.362 min, m/z 227.2 [M+H]$^+$; HRMS (ESI), RT=0.579 min, m/z 227.0712 [M+H]$^+$, formula $C_{14}H_{10}O_3$.

To a solution of 2-ethynyl-5-(phenoxymethyl)furan (1 g, 5.05 mmol) in dry THF at −80° C. was added dropwise 2.5M solution of BuLi in hexane (2.1 ml, 5.55 mol). Resulted solution was stirred for 30 min. at −80° C. Then methyl chloroformate (0.52 g, 5.55 mmol) in THF was added to reaction mixture and left to stir for 1 h, and then slowly warmed to r.t. After 30 min, mixture was quenched by $NH_4Cl$ solution and extracted with EtOAc (20 mL×3). Organic layers were combined, washed with water (10 mL×2) and brine (10 mL), dried over $Na_2SO_4$ and evaporated in vacuo to give crude 1 g of methyl 3-(5-(phenoxymethyl)furan-2-yl)propiolate (MMA-411), which then was used without purification. After column chromatography (Hex:EtOAc=4:1) MMA-411 was obtained as an yellow solid (0.148 g, 0.57 mmol). Yield: 11.5%, $^1$H NMR (400 MHz, DMSO-$d_6$) δ 7.38-7.23 (m, 3H), 7.04 (s, 2H), 7.00-6.93 (m, 1H), 6.79 (d, J=3.5 Hz, 1H), 5.13 (s, 2H), 3.79 (s, 3H). $^{13}$C NMR (126 MHz, DMSO-$d_6$) δ 158.12, 155.65, 153.60, 133.61, 130.03, 123.61, 121.71, 115.22, 112.73, 86.37, 76.63, 61.79, 53.65. LC-MS (ESI), RT=4.09 min, m/z 257.0 [M+H]$^+$; HRMS (ESI), RT=6.756 min, m/z 257.0816 [M+H]$^+$, formula $C_{15}H_{12}O_4$.

Results and Discussion: The syntheses of various novel 5-HMF derivatives with non-aldehyde reactive moieties that are metabolically stable and capable of forming stable covalent interactions with Hb are reported below and grouped into 3 classes of derivatives (Michael Acceptors, α-Ketocarbonyls and 2,2,2-Trifluoroethanone).

A. Michael Acceptors

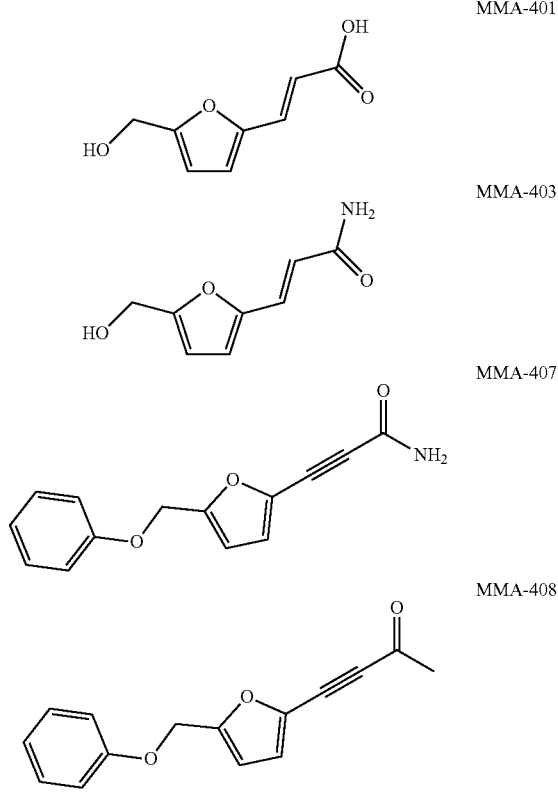

MMA-409

MMA-410

MMA-411

B. α-Ketocarbonyls

MMA-302

MMA-303

MMA-304

MMA-305

C. 2,2,2-Trifluoroethanone

MMA-405

Example 2. Testing of Exemplary Compounds

In Vitro Hemoglobin Modification, Oxygen Equilibrium and Antisickling Studies Using Human Homozygous Sickle Cell (SS) Blood Materials and General Procedure: Leftover blood samples from patients with homozygous SS were obtained and utilized, based on an approved IRB protocol at the Children's Hospital of Philadelphia, with informed consent.

Experimental Procedure: The MMA series of compounds (MMA-301, MMA-304, MMA-205, MMA-401, MMA-402, MMA-403, MMA-405, MMA-406, MMA-407, MMA-408, MMA-409 and MMA-410) and the positive controls vanillin and 5-HMF were studied for their abilities to inhibit hypoxia-induced RBC sickling (RBC morphology study), increase Hb oxygen, and/or modify Hb (adduct formation) as previously published.[31,33] Briefly, homozygous SS blood (hematocrit: 20%) suspensions were incubated under air in the absence or presence of 2 and/or 5 mM concentration of test compounds at 37° C. for 1 hr. Following, the suspensions were incubated under hypoxic condition (2.5% oxygen) at 37° C. for 2 hr. Aliquot samples were fixed with 2% glutaraldehyde solution without exposure to air, and then subjected to microscopic morphological analysis. The residual samples were washed in phosphate-buffered saline, and hemolyzed in hypotonic lysis buffer for the Hb oxygen equilibrium and Hb adduct experiments. For the Hb oxygen equilibrium study, approximately 100 μl aliquot samples from the lysate were added to 4 ml of 0.1M potassium phosphate buffer, pH 7.0, in a cuvette and subjected to hemoximetry analysis using Hemox™ Analyzer (TCS Scientific Corp.) to assess $P_{50}$ shifts. Another aliquot from the lysate was also subjected to Hb adduct formation study using cation-exchange HPLC (Hitachi D-7000 Series, Hitachi Instruments, Inc., San Jose, Calif.) with a weak cation-exchange column (Poly CAT A: 30 mm×4.6 mm, Poly LC, Inc., Columbia, Md.). To determine the binding of the MMA compounds to either α- or β-globin chains, the hemolysates were subjected to reversed-phase (RP) HPLC on a Hitachi D-7000 HSM Series, using a Jupiter 5 μm C-4 50×4.6 mm column, (Phenomenex®, Torrence, Calif.) and a gradient from 20% to 60% acetonitrile in 0.3% trifluoroacetic acid in 15 minutes, with UV detection at 215 nm.

Figure 2:
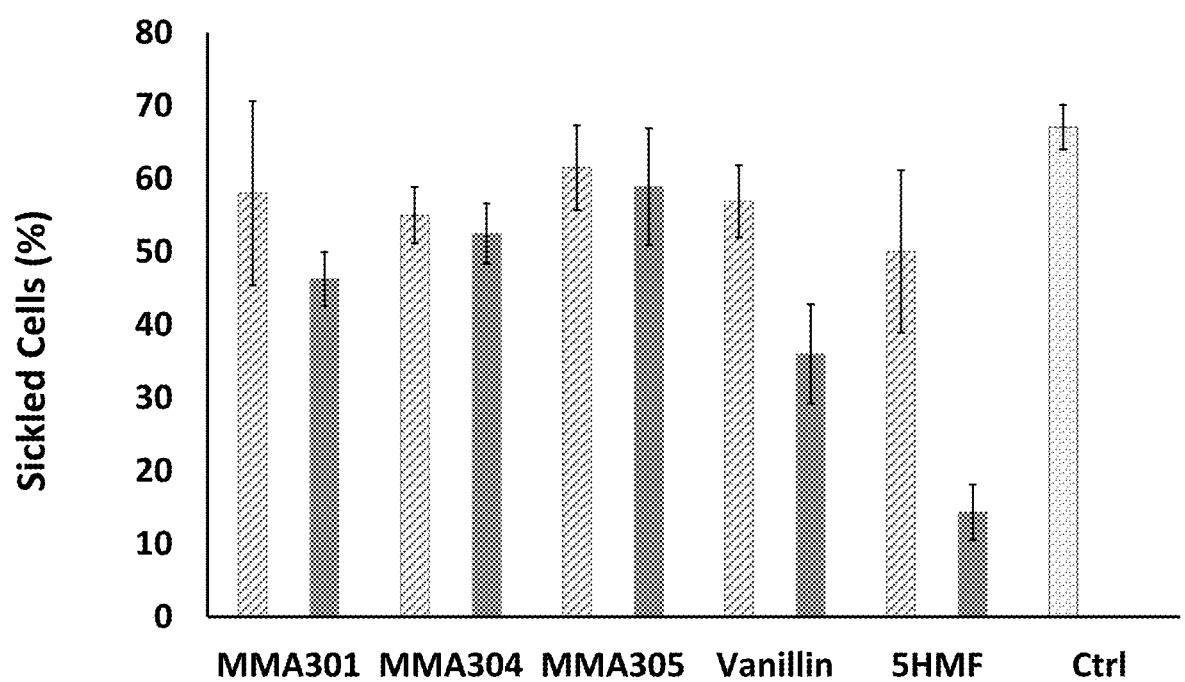
FIG. 2. Antisickling effect of MMA-300 series of compounds on intact SS cells. Diagonal line bar and solid bar denote compound concentrations of 2 mM and 5 mM, respectively. Weave bar denotes control (no compound). N=2 to 8.
Figure 3:
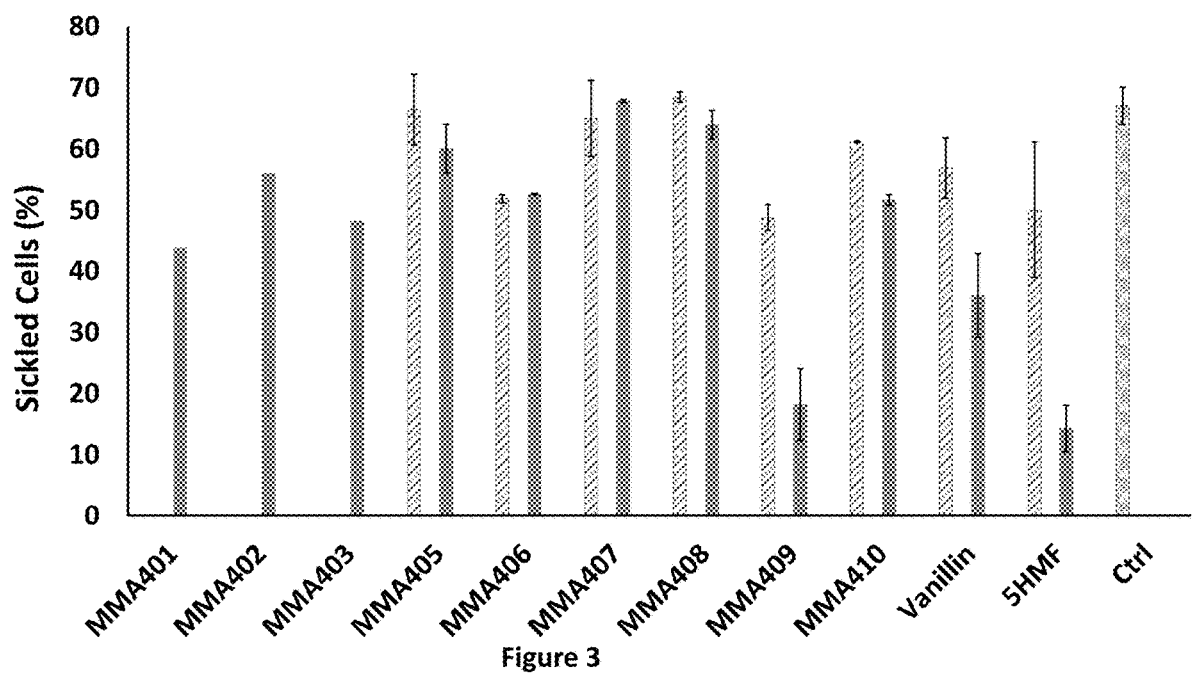
FIG. 3. Antisickling effect of MMA-400 series of compounds on intact SS cells. Diagonal line bar and solid bar denote compound concentrations of 2 mM and 5 mM, respectively. Weave bar denotes control (no compound). n=2 to 8.
Figure 4A:
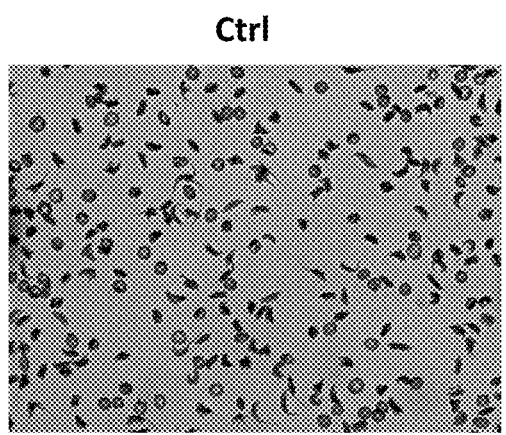
FIGS. 4A-B. Image of Sickled Cells in the (A) absence or (B) presence of MMA-409 under 2.5% $O_2$ Gas.
Figure 4B:
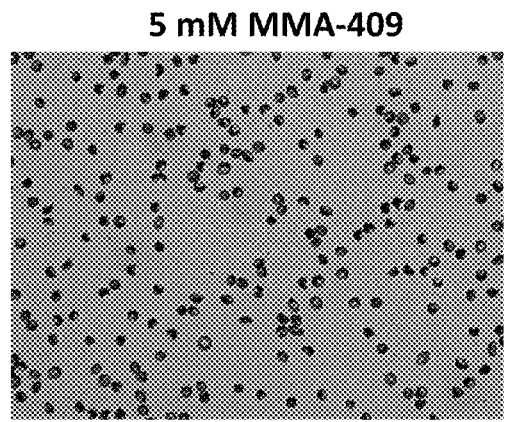
Figure 5:
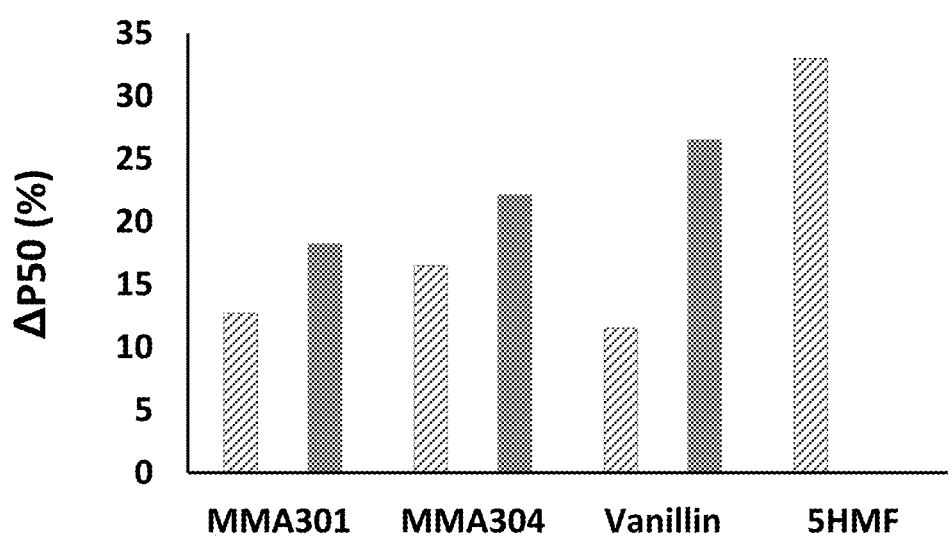
FIG. 5. Degree of shift in Hb oxygen affinity ($\Delta P_{50}$) by MMA-300 series of compounds on intact SS cells (n=2). Solid and pattern bars denote compound concentrations of 2 mM and 5 mM, respectively.

Results and Discussion: The following MMA compounds, MMA-301, MMA-304, MMA-205, MMA-401, MMA-402, MMA-403, MMA-405, MMA-406, MMA-407, MMA-408, MMA-409 and MMA-410 were tested for their effect on Hb modification, Hb oxygen affinity and/or inhibition of RBC sickling at 2 mM and/or 5 mM as previously reported,[31,33] and the results presented in FIGS. 2-9. MMA-409 appears to be the most promising antisickling compound by reducing RBC sickling in a dose-dependent manner to 49% and 18% at 2 mM and 5 mM, respectively (FIGS. 3 and 4). This compares with 50% and 14% by 5-HMF, and 57% and 36% by vanillin, respectively. FIG. 4 is a representative image of sickled cells under 2.5% $O_2$ gas in the presence of MMA-409, and clearly shows MMA-409 to inhibit hypoxia-induced sickling. The rest of the compounds showed weak to no antisickling activities (FIGS. 2 and 3). It appears that among the different reactive moieties, terminal propenoyl, which is unique in MMA-409 is the most reactive in binding and modifying Hb activity.

Figure 6:
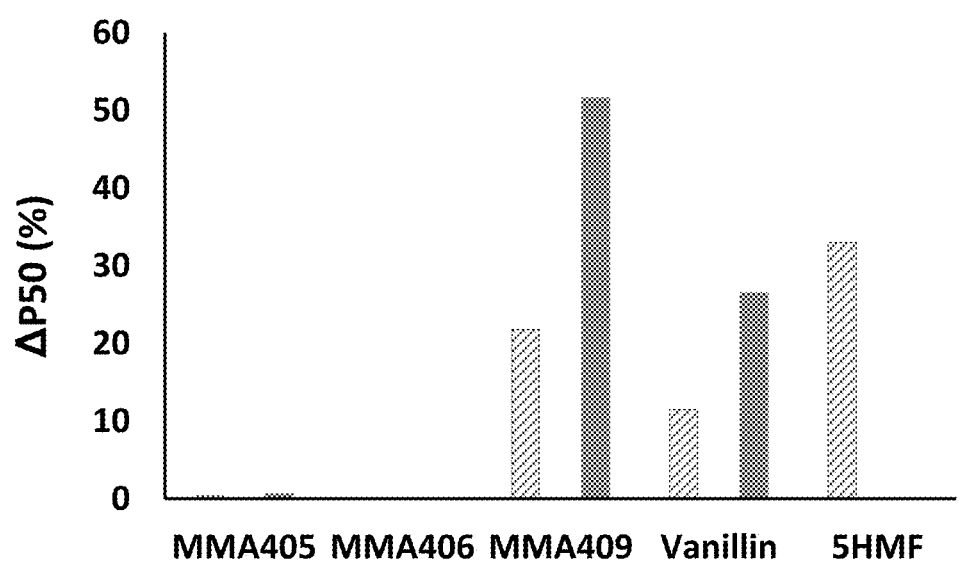
FIG. 6. Degree of shift in Hb oxygen affinity ($\Delta P_{50}$) by MMA-400 series of compounds on intact SS cells (n=2). Solid and pattern bars denote compound concentrations of 2 mM and 5 mM, respectively.
Figure 7:
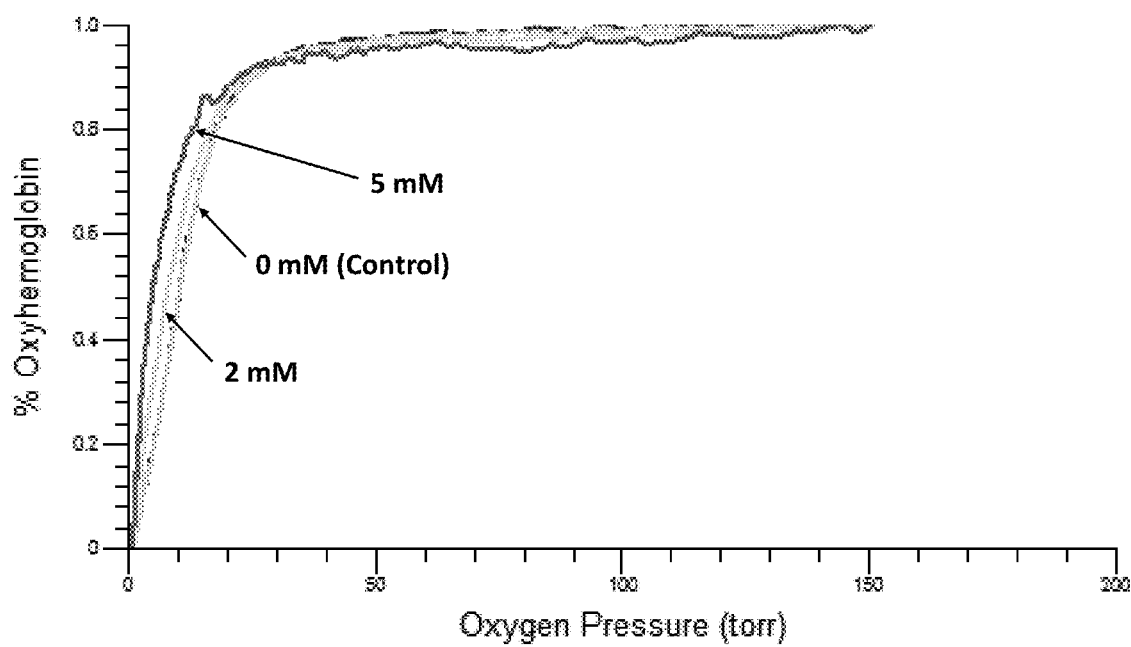
FIG. 7. Oxygen equilibrium curve of 0 mM (control), 2 mM, and 5 mM MMA-409 of intact SS cells.
Figure 8:
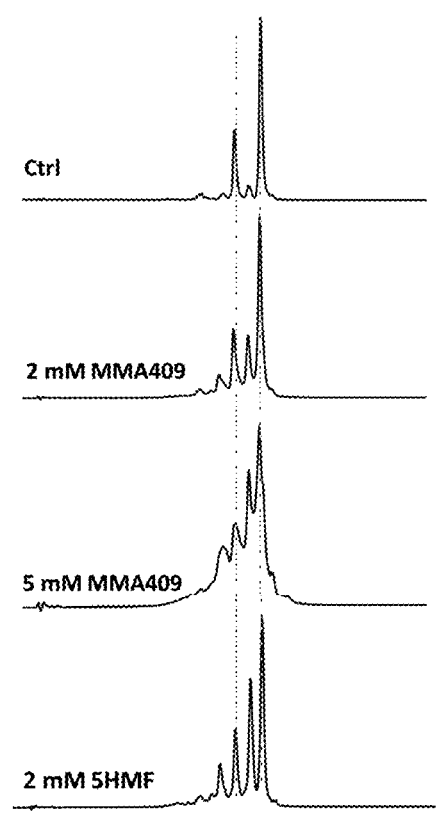
FIG. 8. Cation exchange HPLC of 0 mM (control), 2 mM and/or 5 mM of MMA-409, and 5-HMF after incubation with intact SS Cells.
Figure 9:
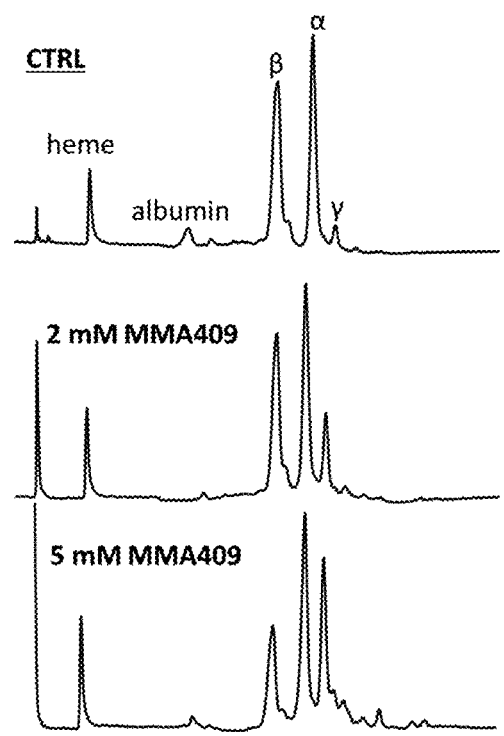
FIG. 9. Reverse-phase HPLC of 0 mM (control), 2 mM and 5 mM of MMA-409 after incubation with intact SS cells.

We also tested the compounds for their effect on Hb modification and Hb oxygen affinity (at 2 mM and/or 5 mM) using aliquot samples from the same incubation sample used for the above antisickling study and the results shown in FIGS. 5-9. As expected from MMA-409 antisickling activity, we observed significant increase in Hb oxygen affinity in dose-dependent manner (22% at 2 mM and 52% at 5 mM) (FIGS. 6 and 7), as well as significant Hb modification for this compound (FIG. 7). This compares with 12% and 27% by vanillin, respectively, and 33% by 5-HMF at 2 mM. Interestingly, MMA-301 (12.7% and 18.2%) and MMA-304 (16.5% and 22.1%), respectively showed moderate increase in Hb oxygen affinity in dose-dependent manner (FIG. 5), although not reflected in their antisickling potencies (FIG. 2). As expected from their lack of antisickling potency, MMA-405 and MMA-406 showed no effect on Hb affinity for oxygen (FIG. 6).

A reverse-phase HPLC study conducted with the most promising MMA compounds MMA-409 showed exclusive adduct formation with the β-chain (FIG. 9), suggesting that in most part these compounds effect their biological activities by binding to the β-chain.

Reactivity of MMA-409 and MMA-410 Toward βCys93 of Hb

Experimental Procedure: Aqueous solution of Hb (50 μM) was mixed with MMA 409 or MMA 410 (2 mM). Additionally, Hb was mixed with phosphate buffered saline (PBS) to serve as a negative control. PBS does not bind to the sulfhydryl groups of hemoglobin. Ethacrynic acid, which is known to bind to the thiols of hemoglobin and thus limits the reaction between DTNB (5,5'-dithiobis-(2-nitrobenzoic acid) and βCys93, was studied as a positive control.[42] The mixtures were incubated for four hours at 25° C., and then centrifuged with washing to separate excess reagents from the Hb. The washed hemoglobin was stored overnight at 4° C. After, 5 μL of 100 mM DTNB was added to 25 μL of each Hb solution, and these solutions were each diluted to 500 μL in 0.1 M phosphate buffer and were incubated for an hour. Another 25 μL of each Hb solution was diluted to 500 μL in buffer to serve as a non-DTNB control. The tubes containing these solutions were centrifuged, and the collected yellow filtrate was quantified by measuring absorbance at 412 nm using a spectrophotometer as previously described.[42]

Figure 10:
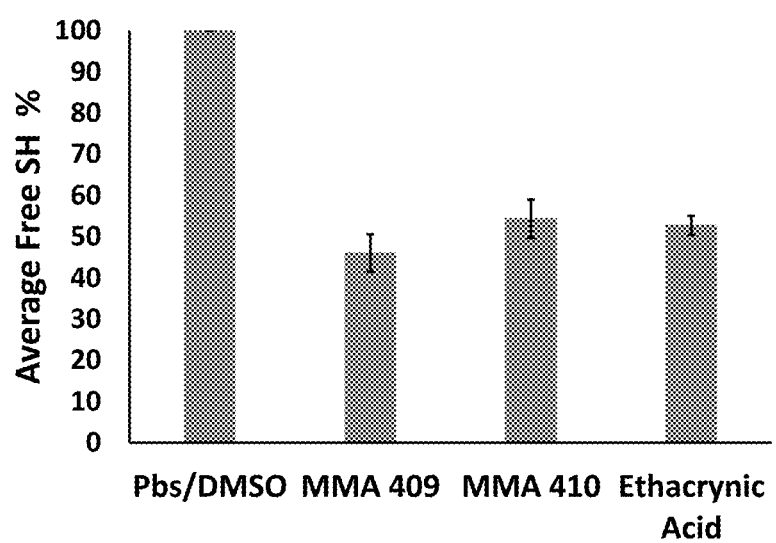
FIG. 10. Reactivity of MMA-409 and MMA-410 (2 mM) with βCys93 of Hb. (n=2).

Results and Discussion: Our design approach envisaged the MMA compounds to bind and form adduct with βCys93 residue, which is consistent with the observation from our reverse-phase HPLC results that showed MMA-409 to modify the β-chain. To determine the compounds potential interaction with βCys93 of Hb, we studied MMA-409 (the most potent antisickling compound) and MMA-410 (one of the least potent antisickling compounds). The reactivity of the MMA compounds with βCys93 was measured through observing the results of the disulfide exchange reaction between DTNB and the thiol of βCys93.[42] The results indicate that in the presence of MMA409 and MMA410, the % free thiols of βCys93 were 46 and 54, respectively (FIG. 10), suggesting interaction of these compounds with βCys93 thiol. These results compare with the negative and positive controls, PBS/DMSO and ethacrynic acid that showed 100% and 54% free thiols, respectively. As previously reported for ECA,[42] compounds that interact with βCys93 destabilize the T-state and shift Hb oxygen equilibrium to the R-state to prevent polymerization and RBC sickling, explaining the antisickling activities of the MMA compounds.

In Vitro Time-Dependent Hb Oxygen Equilibrium Studies Using Normal Whole Blood

Materials and General Procedure: Normal whole blood was collected from adult donors at the Virginia Commonwealth University after informed consent, in accordance with regulations of the IRB for Protection of Human.

Experimental procedure: MMA-409 and the control 5-HMF were used to conduct time-dependent studies on Hb oxygen oxygen equilibrium using normal whole blood. The study was performed in a 96-well deep well (Thermo Scientific) plate, where each compound at 2 mM concentration was added to 600 μL of whole blood (30% hct) and incubated at 37° C. for 24 hr with shaking (at 140 rpm). Additionally, DMSO (1%) alone was also tested as a negative control. At 1, 4 and 24 hr time intervals, 75 μL aliquot of blood was removed from each well using a multichannel pipette and the reaction stopped by freezing at −80° C. until ready for hemoximetry analysis using Hemox™ Analyzer (TCS Scientific Corp.) to assess $P_{50}$ shifts.[32] The observed $P_{50}$ shifts values in % $P_{50}$ shifts were plotted as function of time [hrs].

Figure 11:
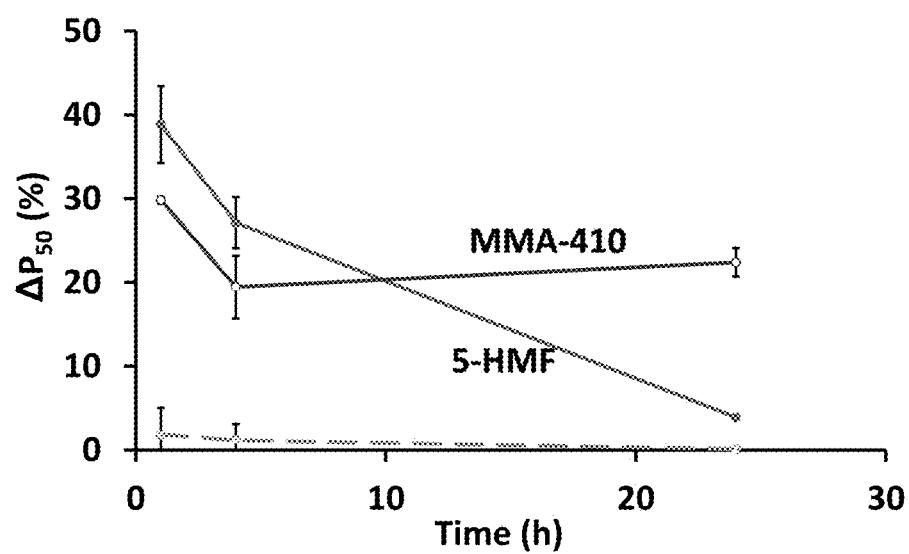
FIG. 11. Time-dependent modification of Hb in normal whole blood incubated with test compounds (n=2). Solid line is 5-HMF, dotted line is MMA-410, and long dash line is DMSO (1%).

Results and Discussion: The main purpose for developing these novel compounds was to improve on the pharmacokinetic properties of the aromatic aldehyde, 5-HMF by replacing the aldehyde moiety of this pharmacophore with a more metabolically stable reactive center to reduce the apparent rapid oxidative metabolism. As noted above, 5-HMF and other aromatic aldehydes suffer from oxidative metabolism by aldehyde dehydrogenase, aldehyde oxidase in the liver, blood and other tissues that leads to short half-life and suboptimal bioavailability.[31,33,45,46] The in vitro time-dependent Hb oxygen equilibrium studies with MMA-409 (2 mM drug concentration) using freshly drawn normal whole blood showed that unlike the biological activity of 5-HMF which declined rapidly due to metabolism of the aldehyde, the activity of MMA-409 was sustained throughout the 24 hr experiment (FIG. 11). This is a significant improvement in the compound duration of action. Blood contains enzymes that are known to metabolize aromatic aldehydes and other compounds, and is a good predictor of the metabolic stability of compounds.[38-40] Although, other metabolic routes, including the liver could reduce the pharmacologic activity of our novel compounds, we still expect significant improvement in the metabolic profile of these compounds in vivo.

CONCLUSION

Vanillin, 5-HMF and several of their aromatic aldehyde derivatives even though show promising as antisickling agents, their development into therapeutic agents have been hampered by poor PK properties due in most part by the metabolically unstable aldehyde moiety. We have developed novel compounds by derivatization of the 5-HMF pharmacophore with a metabolically stable reactive centers that not only showed equipotency as 5-HMF, but most importantly, these compounds show improved in vitro metabolic profile, with MMA-409 clearly the most superior. Improved PK properties should translate into effective lower therapeutic dose.

ACKNOWLEDGMENT

This project was funded by the National Plan for Science, Technology, and Innovation (MAARIFAH), King Abdulaziz City for Science and Technology, the Kingdom of Saudi Arabia; Award number 14-BIO80-03. The authors also, acknowledge with thanks Science and Technology Unit, King Abdulaziz University, for technical support.

REFERENCES

1. Aliyu, Z. Y. et al. Prevalence and risk factors for pulmonary artery systolic hypertension among sickle cell disease patients in Nigeria. *Am. J. Hematol.* 83, 485-490 (2008).
2. Piel, F. B., Steinberg, M. H. & Rees, D. C. Sickle Cell Disease. *N. Engl. J. Med.* 377, 305 (2017).
3. Poillon, W. N. & Kim, B. C. 2,3-Diphosphoglycerate and intracellular pH as interdependent determinants of the physiologic solubility of deoxyhemoglobin S. *Blood* 76, 1028-1036 (1990).

4. Poillon, W. N., Kim, B. C., Labotka, R. J., Hicks, C. U. & Kark, J. A. Antisickling effects of 2,3-diphosphoglycerate depletion. *Blood* 85, 3289-3296 (1995).
5. Poillon, W. N., Kim, B. C., Welty, E. V. & Walder, J. A. The effect of 2,3-diphosphoglycerate on the solubility of deoxyhemoglobin S. *Arch. Biochem. Biophys.* 249, 301-305 (1986).
6. Sun, K. et al. Structural and Functional Insight of Sphingosine 1-Phosphate-Mediated Pathogenic Metabolic Reprogramming in Sickle Cell Disease. *Sci Rep* 7, 15281 (2017).
7. Sun, K. et al. Sphingosine-1-phosphate promotes erythrocyte glycolysis and oxygen release for adaptation to high-altitude hypoxia. *Nat Commun* 7, 12086 (2016).
8. Zhang, Y. et al. Elevated sphingosine-1-phosphate promotes sickling and sickle cell disease progression. *J. Clin. Invest.* 124, 2750-2761 (2014).
9. Zhang, Y. et al. Detrimental effects of adenosine signaling in sickle cell disease. *Nat. Med.* 17, 79-86 (2011).
10. Ghatge, M. S. et al. Crystal structure of carbonmonoxy sickle hemoglobin in R-state conformation. *J. Struct. Biol.* 194, 446-450 (2016).
11. Ferrone, F. A. & Rotter, M. A. Crowding and the polymerization of sickle hemoglobin. *J. Mol. Recognit.* 17, 497-504 (2004).
12. Cretegny, I. & Edelstein, S. J. Double strand packing in hemoglobin S fibers. *J. Mol. Biol.* 230, 733-738 (1993).
13. Eaton, W. A. & Hofrichter, J. Sickle cell hemoglobin polymerization. *Adv. Protein Chem.* 40, 63-279 (1990).
14. Harrington, D. J., Adachi, K. & Royer, W. E. The high resolution crystal structure of deoxyhemoglobin S. *J. Mol. Biol.* 272, 398-407 (1997).
15. Bunn, F. Molecular, Genetic and Clinical Aspects. in *In Hemoglobin:* 502-564 (W. B. Saunders company, 1986).
16. Akinsheye, I. & Klings, E. S. Sickle cell anemia and vascular dysfunction: the nitric oxide connection. *J. Cell. Physiol.* 224, 620-625 (2010).
17. De Franceschi, L. Pathophisiology of sickle cell disease and new drugs for the treatment. *Mediterr J Hematol Infect Dis* 1, e2009024 (2009).
18. Belcher, J. D. et al. Transgenic sickle mice have vascular inflammation. *Blood* 101, 3953-3959 (2003).
19. Mvalo, T. et al. Increasing hydroxyurea use in children with sickle cell disease at Kamuzu Central Hospital, Malawi. *Blood Adv* 2, 30-32 (2018).
20. Brandow, A. M. & Panepinto, J. A. Hydroxyurea use in sickle cell disease: the battle with low prescription rates, poor patient compliance and fears of toxicities. *Expert Rev Hematol* 3, 255-260 (2010).
21. Sinha, C. B., Bakshi, N., Ross, D. & Krishnamurti, L. From trust to skepticism: An in-depth analysis across age groups of adults with sickle cell disease on their perspectives regarding hydroxyurea. *PloS one* 13, e0199375 (2018).
22. L-glutamine (Endari) for sickle cell disease. *Med Lett Drugs Ther* 60, 21-22 (2018).
23. Kaufman, M. Pharmaceutical approval update: L-glutamine oral powder (Endari). *Pharmacy and Therapeutics* 42, 620-21 (2017).
24. Cieri-Hutcherson, N. E., Hutcherson, T. C., Conway-Habes, E. E., Burns, B. N. & White, N. A. Systematic Review of l-glutamine for Prevention of Vaso-occlusive Pain Crisis in Patients with Sickle Cell Disease. *Pharmacotherapy* (2019) doi:10.1002/phar.2329.
25. Ataga, K. I. et al. Crizanlizumab for the prevention of pain crises in sickle cell disease. *New England Journal of Medicine* 376, (2017).
26. Vichinsky, E. et al. A Phase 3 randomized trial of voxelotor in sickle cell disease. *New England Journal of Medicine* (2019) doi:10.1056/NEJMoa1903212.
27. Oder, E., Safo, M. K., Abdulmalik, O. & Kato, G. J. New developments in anti-sickling agents: can drugs directly prevent the polymerization of sickle haemoglobin in vivo?*British Journal of Haematology* vol. 175 24-30 (2016).
28. Safo, M. K. & Kato, G. J. Therapeutic strategies to alter the oxygen affinity of sickle hemoglobin. *Hematology/Oncology Clinics of North America* (2014) doi:10.1016/j.hoc.2013.11.001.
29. Safo, M. K. & Bruno, S. Allosteric Effectors of Hemoglobin: Past, Present and Future. in *Chemistry and Biochemistry of Oxygen Therapeutics: From Transfusion to Artificial Blood* (eds. Mozzarelli, A. & and Bettati, S.) 285-300 (John Wiley & Sons, Ltd, 2011).
30. Safo, M. K., Ahmed, M. H., Ghatge, M. S. & Boyiri, T. Hemoglobin-ligand binding: understanding Hb function and allostery on atomic level. *Biochim. Biophys. Acta* 1814, 797-809 (2011).
31. Abdulmalik, O. et al. 5-Hydroxymethyl-2-furfural modifies intracellular sickle haemoglobin and inhibits sickling of red blood cells. *British Journal of Haematology* 128, 552-561 (2005).
32. Xu, G. G. et al. Design, Synthesis, and Biological Evaluation of Ester and Ether Derivatives of Antisickling Agent 5-HMF for the Treatment of Sickle Cell Disease. *Molecular Pharmaceutics* (2017) doi:10.1021/acs.molpharmaceut.7b00553.
33. Safo, M. K. et al. Structural Basis for the Potent Antisickling Effect of a Novel Class of Five-Membered Heterocyclic Aldehydic Compounds. *J. Med. Chem.* 47, 4665-4676 (2004).
34. Abdulmalik, O. et al. Crystallographic analysis of human hemoglobin elucidates the structural basis of the potent and dual antisickling activity of pyridyl derivatives of vanillin. *Acta Crystallographica Section D: Biological Crystallography* vol. 67 920-928 (2011).
35. Deshpande, T. M. et al. Rational modification of vanillin derivatives to stereospecifically destabilize sickle hemoglobin polymer formation. *Acta Crystallographica Section D: Structural Biology* 74, 956-964 (2018).
36. Pagare, P. P. et al. Rational design of pyridyl derivatives of vanillin for the treatment of sickle cell disease. *Bioorg. Med. Chem.* 26, 2530-2538 (2018).
37. Nnamani, I. N. et al. Pyridyl derivatives of benzaldehyde as potential antisickling agents. *Chem. Biodivers.* 5, 1762-1769 (2008).
38. Godfrey, V. B., Chen, L. J., Griffin, R. J., Lebetkin, E. H. & Burka, L. T. Distribution and metabolism of (5-hydroxymethyl)furfural in male F344 rats and B6C3F1 mice after oral administration. *J. Toxicol. Environ. Health Part A* 57, 199-210 (1999).
39. Yoshida, A., Rzhetsky, A., Hsu, L. C. & Chang, C. Human aldehyde dehydrogenase gene family. *Eur. J. Biochem.* 251, 549-557 (1998).
40. Vasiliou, V., Pappa, A. & Petersen, D. R. Role of aldehyde dehydrogenases in endogenous and xenobiotic metabolism. *Chem. Biol. Interact.* 129, 1-19 (2000).
41. Abdulmalik, O. et al. MSDD1, a prodrug of 5-Hydroxymethyl-2-Furfural (5HMF), prolongs the antisickling effect of 5HMF in Transgenic Sickle Mice. Proceedings of the 28th Annual meeting of the National Sickle Cell Disease Program. in (2005).

42. Omar, A. M. et al. Identification of a novel class of covalent modifiers of hemoglobin as potential antisickling agents. *Org. Biomol. Chem.* 13, 6353-6370 (2015).
43. Nakagawa, A. et al. A Triazole Disulfide Compound Increases the Affinity of Hemoglobin for Oxygen and Reduces the Sickling of Human Sickle Cells. *Mol. Pharm.* 15, 1954-1963 (2018).
44. Nakagawa, A. et al. Identification of a small molecule that increases hemoglobin oxygen affinity and reduces SS erythrocyte sickling. *ACS Chem. Biol.* 9, 2318-2325 (2014).
45. Obied &, T., Venitz, J. 5-hydroxy methyl furfural (5-HMF) metabolism in hepatic cytosol from mice, rats, dogs, and humans. in 23 *rd Annual Meeting* (The AAPS Journal, 2009).
46. Abraham, D. J. et al. Vanillin, a potential agent for the treatment of sickle cell anemia. *Blood* 77, 1334-1341 (1991).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating a hypoxia-associated disease or condition or treating sickle cell disease in a subject in need thereof, comprising administering to the subject a therapeutically effective amount of a compound, or pharmaceutically acceptable salt or solvate thereof, wherein the compound is selected from the group consisting of

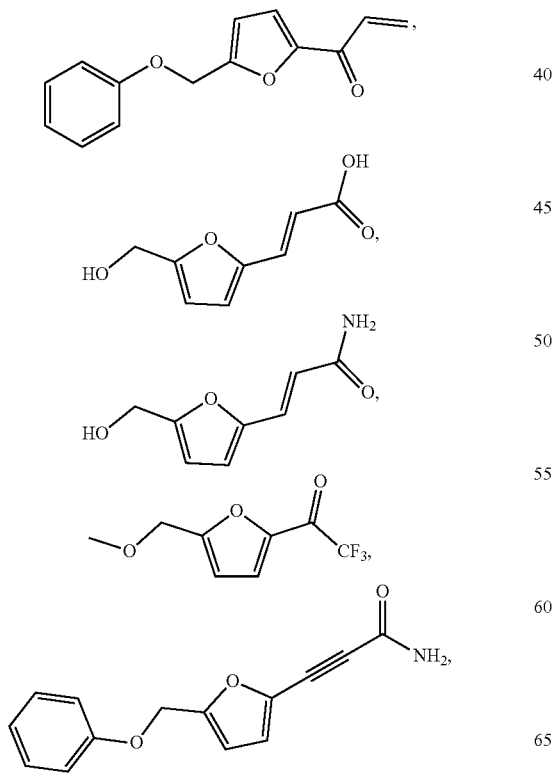

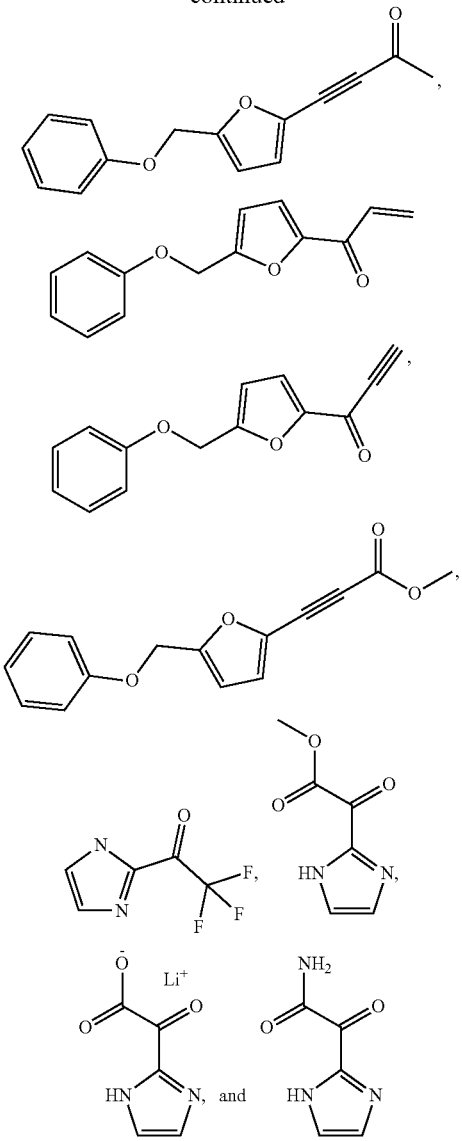

wherein the hypoxia-associated disease or condition is selected from the group consisting of acute respiratory distress syndrome (ARDS), hemorrhagic shock, traumatic shock, cardiac arrest, cardiogenic shock, traumatic brain injury, stroke, cancer, myocardial infarction, myocardial ischemia, and vaso-occlusive crisis.

2. A method of treating a hypoxia-associated disease or condition or treating sickle cell disease in a subject in need thereof, comprising administering to the subject a therapeutically effective amount of a compound, or pharmaceutically acceptable salt or solvate thereof, wherein the compound is selected from the group consisting of

MMA-401

-continued

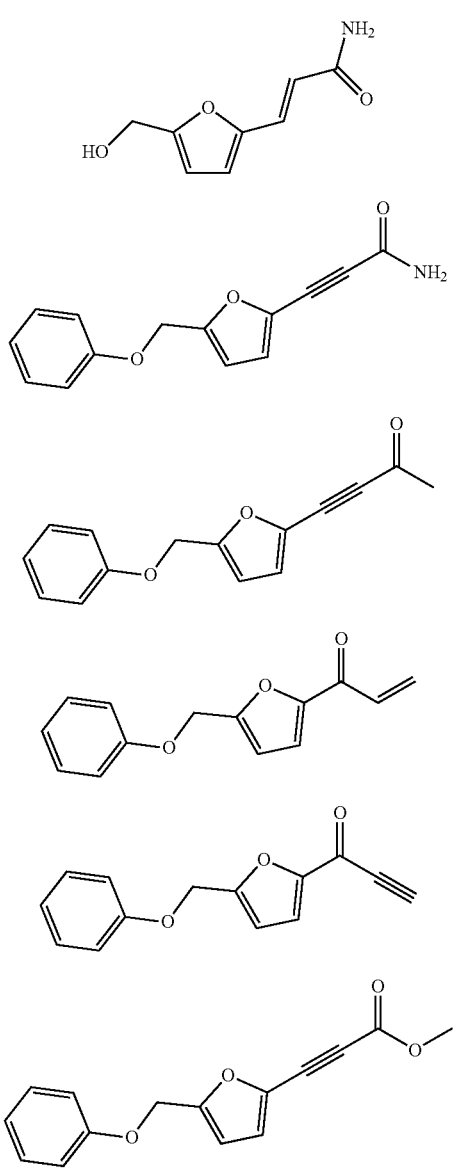

MMA-403

MMA-407

MMA-408

MMA-409

MMA-410

MMA-411 wherein the hypoxia-associated disease or condition is selected from the group consisting of acute respiratory distress syndrome (ARDS), hemorrhagic shock, traumatic shock, cardiac arrest, cardiogenic shock, traumatic brain injury, stroke, cancer, myocardial infarction, myocardial ischemia, and vaso-occlusive crisis.

3. A method of treating a hypoxia-associated disease or condition or treating sickle cell disease in a subject in need thereof, comprising administering to the subject a therapeutically effective amount of a compound, or pharmaceutically acceptable salt or solvate thereof, wherein the compound is selected from the group consisting of

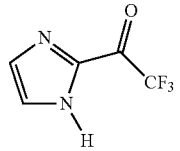

MMA-302

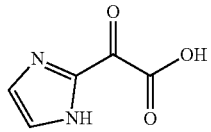

MMA-303

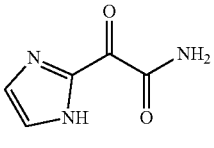

MMA-304

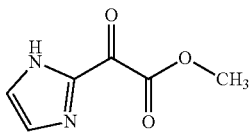

MMA-305 wherein the hypoxia-associated disease or condition is selected from the group consisting of acute respiratory distress syndrome (ARDS), hemorrhagic shock, traumatic shock, cardiac arrest, cardiogenic shock, traumatic brain injury, stroke, cancer, myocardial infarction, myocardial ischemia, and vaso-occlusive crisis.

4. A method of treating a hypoxia-associated disease or condition or treating sickle cell disease in a subject in need thereof, comprising administering to the subject a therapeutically effective amount of a compound, or pharmaceutically acceptable salt or solvate thereof, wherein the compound is

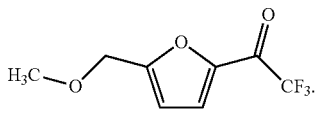

MMA-405 wherein the hypoxia-associated disease or condition is selected from the group consisting of acute respiratory distress syndrome (ARDS), hemorrhagic shock, traumatic shock, cardiac arrest, cardiogenic shock, traumatic brain injury, stroke, cancer, myocardial infarction, myocardial ischemia, and vaso-occlusive crisis.

* * * * *